US012667296B2

(12) United States Patent
Riekkinen et al.

(10) Patent No.: US 12,667,296 B2
(45) Date of Patent: Jun. 30, 2026

(54) ADJUSTMENT OF LONG TERM INTRAINDIVIDUAL CHANGES IN PRECORDIAL ECG AMPLITUDES

(71) Applicant: BIOPOTENTIAL Oy Ltd, Kuopio (FI)

(72) Inventors: Heikki Riekkinen, Kuopio (FI);
Tommi Riekkinen, Kuopio (FI);
Annika Kolari, Kuopio (FI)

(73) Assignee: BIOPOTENTIAL Oy Ltd, Kuopio (FI)

( * ) Notice: Subject to any disclaimer, the term of this patent is extended or adjusted under 35 U.S.C. 154(b) by 469 days.

(21) Appl. No.: 18/265,253

(22) PCT Filed: Dec. 2, 2021

(86) PCT No.: PCT/EP2021/084034
§ 371 (c)(1),
(2) Date: Jun. 4, 2023

(87) PCT Pub. No.: WO2022/117755
PCT Pub. Date: Jun. 9, 2022

(65) Prior Publication Data
US 2024/0041380 A1      Feb. 8, 2024

(51) Int. Cl.
*A61B 5/352* (2021.01)
*A61B 5/30* (2021.01)
(Continued)

(52) U.S. Cl.
CPC .............. *A61B 5/352* (2021.01); *A61B 5/303* (2021.01); *A61B 5/338* (2021.01); *A61B 5/366* (2021.01)

(58) Field of Classification Search
CPC ......... A61B 5/352; A61B 5/338; A61B 5/303; A61B 5/366
(Continued)

(56) References Cited

FOREIGN PATENT DOCUMENTS

WO      2021/110937 A1      6/2021    ............... A61B 5/26

OTHER PUBLICATIONS

Kliegfield PG et al.: Recommendations for the standardization and interpretation of electrocardiogram. J Am Coll Cardiol. 2007, 49: 1109-27.

(Continued)

*Primary Examiner* — Nadia A Mahmood
(74) *Attorney, Agent, or Firm* — Bauer & Joseph

(57) ABSTRACT

The present disclosure lies in the general field of clinical electrocardiography (ECG), more specifically in ECG methods comprising precordial ECG amplitude measurements. The present invention relates to methods of determining a subject's corrected precordial ECG amplitude from an ECG measurement, which corrections are based on intraindividual changes such as the rotation position of the heart on the horizontal plane, and/or changes in body mass index. The methods are thus useful for adjustment of intraindividual changes over time in precordial ECG amplitudes, such as between two ECG measurements. The present invention further relates to a device, an apparatus and a computer program product, and to uses of said device, apparatus and computer program product in a method of determining a subject's corrected precordial ECG amplitude from an ECG measurement, and for improving the accuracy of electrocardiographic methods depending on precordial ECG amplitude measurements. For example, the methods and the device, apparatus or product can be advantageously used in a method of diagnosing left ventricular hypertrophy and/or hypertension in a subject.

4 Claims, 6 Drawing Sheets

(51) Int. Cl.
    *A61B 5/338*        (2021.01)
    *A61B 5/366*        (2021.01)
(58) Field of Classification Search
    USPC ........................................................ 600/521
    See application file for complete search history.

(56)                References Cited

OTHER PUBLICATIONS

Schijvenaars Bja et al.: Intraindividual variability in electrocardio-grams. J Electrocardiol. J Electrocardiol 2008; 41: 190-196.
Van Oosterom A et al.: Geometrical factors affecting the interindividual varability of the ECG and VCG. J Electrocardiol. 2000; 33: 219-227.
Aro et al., Delayed QRS transition in the precordial leads of an electrocardiogram as a predictor of sudden cardiac death in the general population. Heart Rhythm 2014; 11:2254-2260.
Prineas RJ et al: Distribution and determinants of QRS rotation of black and white persons in the general population. J Electrocardiol 2018; 51: 316-322.
Harlan et al., Serial electrocardiograms: Their reliability and prognastic validity during a 24-yr period. J. Chron. Dis. 1967; 20:853-867.
Fowler NB et Braunstein JR.: Anatomic and electrocardiogram of the heart. Circulation 1951; 3: 906-910.
Bradford N et al. Abnormal electrocardiogramansition zone and risk of mortality in individuals free of of cardiovascular disease. Europace 2015; 17: 131-136.
Search Report and Written Opinion, PCT Application No. EP2021/084034, Feb. 25, 2022.
Patel S et al.: Counterclockwise and clockwise rotation of QRS transition zone: prospective correlates of change and time-varying associations with cardiovascular outcomes. J Am Heart Assoc. 2017; 6: 1-9.
Okin PM et al.: Effect of obesity on electrocardiogramtricular hypertrophy in hypersensitive patients. Hypertension 2000; 36: 13-18.
Fontana L and Hu FB.: Optimal body weight for health and longevity: bridging basic, clinical and population research. Aging Cell 2014; 13: 391-400.
Rider et al.: Improvement in ECG accuracy for diagnosis of left ventricular hypertrophy in obesity. Heart 2016; 102: 1566-1572.
Nakamura Y.: Prognostic values of clockwise and counterclockwise rotation for cardiovascular mortality in japanese subjects, A 24-year follow-up of the national integrated project for prospective obser-vation of noncommunicable disease and its trends in the aged. 1980-2004 (Nippon Data 80). Circulation. 2012; 125: 1226-1233.
Cuspidi C et al.: Does QRS voltage correction by body mass index improve the accuracy of electrocardiogram detecting left ventricular hypertrophy and predicting cardiovascular events in general popu-lation? The Journal of Clinical Hypertension 2016; 5: 415-421.
Snelder S, van d Poll S, de Groot L et al.: Optimized electrocardiogramia for the detection of left ventricular hypertrophy in obesity patients, Clin Cardiol. 2020; 43: 483-490.
Abächerli R et al.: Correlation relationship assesment between left ventricular hypertrophy voltage criteria and body mass index in 41,806 swiss conscripts. Ann. Noninvasive Electrocardiol 2009; 14: 381-388.
Tahara Y et al.: Evaluation of the electrocardiogramsitional zone by cardiac computer tomography. J Electrocardiol. 1991; 24: 239-45.
Horton JD et al.: Distance correction for precordial electrocardio-gram estimating left ventricular mass. Circulation 1977; 55: 509-512.
Hassing GJ et al. Body mass index related electrocardiogramdings in healthy young individuals with a normal body mass index. Neth Heart J 2019; 27: 506-512.
Tafeit E et al.: Using body mass index ignores the intensive training of elite special force personnel. Experimental Biology and Medicine 2019; 244: 873-879.
Kurisu S et al.: Electrocardiogramaracteristics in the underweight and obese in accordance with the World Health Organization classification. 2015; IJC Metabolic § Endocrine 2015; 9: 61-.
Norman JE et al.: Improved detection of echocardiographic left ventricular hypertrophy using a new elecrocardiographic algorithm. J Am Coll Cardiol. 1993; 21: 1680-6.
Sathananthan G et al.: Cardiac orientation: is there a correlation between the anatomical and the electrical axis of the heart. The British Journal of Cardiology 2015; 22: 1-10.

Figure 3

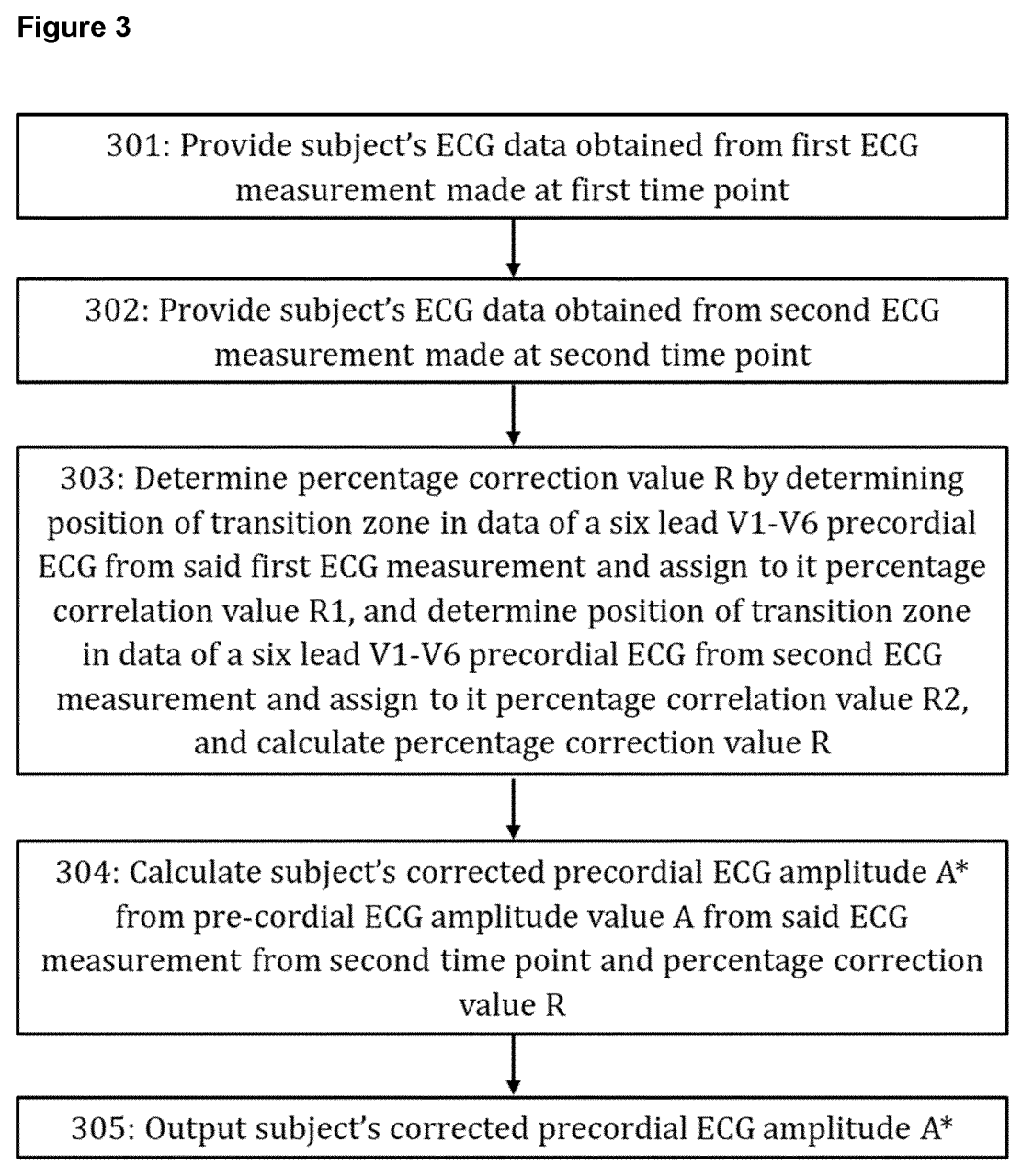

301: Provide subject's ECG data obtained from first ECG measurement made at first time point 302: Provide subject's ECG data obtained from second ECG measurement made at second time point 303: Determine percentage correction value R by determining position of transition zone in data of a six lead V1-V6 precordial ECG from said first ECG measurement and assign to it percentage correlation value R1, and determine position of transition zone in data of a six lead V1-V6 precordial ECG from second ECG measurement and assign to it percentage correlation value R2, and calculate percentage correction value R 304: Calculate subject's corrected precordial ECG amplitude A* from pre-cordial ECG amplitude value A from said ECG measurement from second time point and percentage correction value R 305: Output subject's corrected precordial ECG amplitude A*

Figure 4

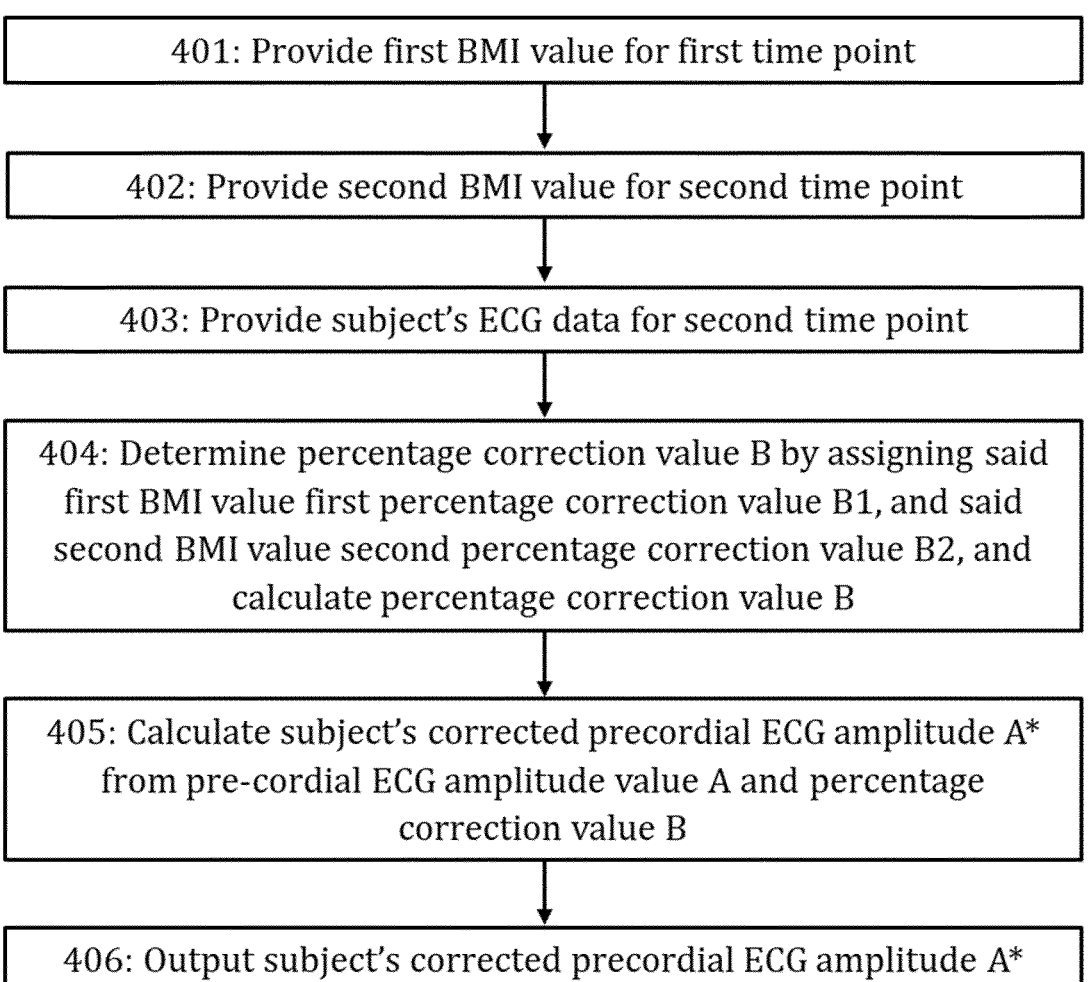

401: Provide first BMI value for first time point

402: Provide second BMI value for second time point

403: Provide subject's ECG data for second time point

404: Determine percentage correction value B by assigning said first BMI value first percentage correction value B1, and said second BMI value second percentage correction value B2, and calculate percentage correction value B 405: Calculate subject's corrected precordial ECG amplitude A* from pre-cordial ECG amplitude value A and percentage correction value B 406: Output subject's corrected precordial ECG amplitude A*

Figure 5

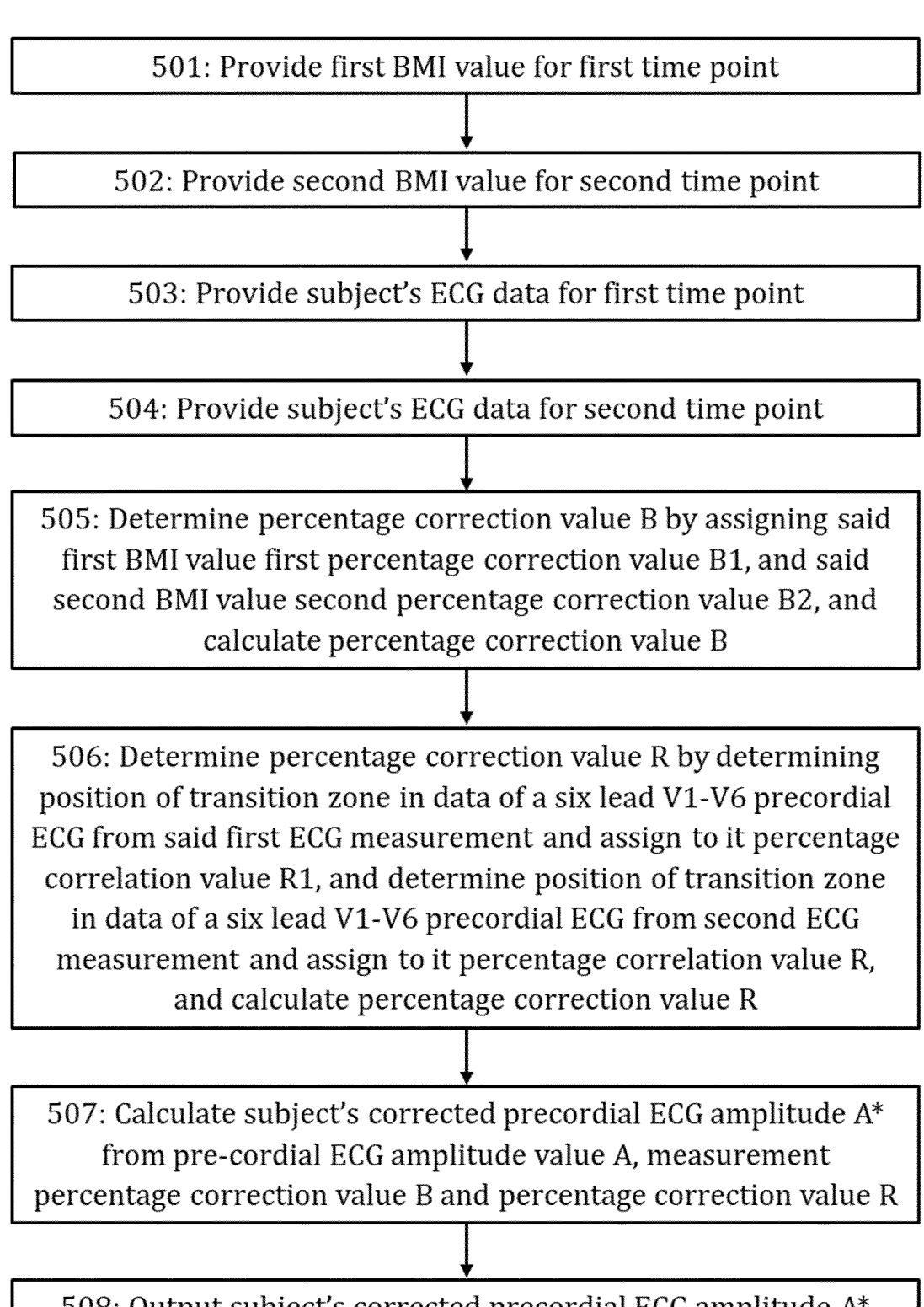

501: Provide first BMI value for first time point

502: Provide second BMI value for second time point

503: Provide subject's ECG data for first time point

504: Provide subject's ECG data for second time point

505: Determine percentage correction value B by assigning said first BMI value first percentage correction value B1, and said second BMI value second percentage correction value B2, and calculate percentage correction value B 506: Determine percentage correction value R by determining position of transition zone in data of a six lead V1-V6 precordial ECG from said first ECG measurement and assign to it percentage correlation value R1, and determine position of transition zone in data of a six lead V1-V6 precordial ECG from second ECG measurement and assign to it percentage correlation value R, and calculate percentage correction value R 507: Calculate subject's corrected precordial ECG amplitude A* from pre-cordial ECG amplitude value A, measurement percentage correction value B and percentage correction value R 508: Output subject's corrected precordial ECG amplitude A*

601

ADJUSTMENT OF LONG TERM INTRAINDIVIDUAL CHANGES IN PRECORDIAL ECG AMPLITUDES

This application is a national stage application under 35 U.S.C. § 371 of PCT Application No. PCT/EP2021/084034 filed on Dec. 2, 2021, which in turn claimed priority to PCT Application No. PCT/EP2020/084668 filed on Dec. 4, 2020.

FIELD OF THE INVENTION

The present disclosure lies in the general field of clinical electrocardiography (ECG), more specifically in ECG methods comprising precordial ECG amplitude measurements. The present invention relates to methods of determining a subject's corrected precordial ECG amplitude from an ECG measurement, which corrections are based on intraindividual changes such as the rotation position of the heart on the horizontal plane, and/or changes in body mass index. The methods are thus useful for adjustment of intraindividual changes over time in precordial ECG amplitudes, such as between two ECG measurements. The present invention further relates to a device, an apparatus and a computer program product, and to uses of said device, apparatus and computer program product in a method of determining a subject's corrected precordial ECG amplitude from an ECG measurement, and for improving the accuracy of electrocardiographic methods depending on precordial ECG amplitude measurements. For example, the methods and the device, apparatus or product can be advantageously used in a method of diagnosing left ventricular hypertrophy and/or hypertension in a subject.

BACKGROUND OF THE INVENTION

Clinical ECG represents the magnitude and direction of the electrical forces generated by the heart as a function of time measured on the subject's body surface. Besides the absolute magnitudes of the individual deflections like P, QRS, and T waves, called amplitudes, also the form of electrocardiogram is dependent on accurate and reproducible measurement of voltage.

ECG is the most commonly used method for clinical heart study in the world (Kligfield et al. 2007). Its great advantages are non-invasiveness, low cost and its easy use. It can be recorded all over the world. The same properties are intended to be included in the method and device of the present invention.

Vertically, the ECG graph measures the height (amplitude) of a given wave or deflection. The amplitude, or voltage, of the recorded electrical signal is expressed on an ECG in the vertical dimension and is measured in millivolts (mV). On standard ECG paper 1 mV is represented by a deflection of 10 mm.

Detection of absolute precordial ECG amplitudes compared to other human beings (interindividual variability) is not possible because of individual differences in congenital factors like, for instance, skeletal dimensions and others, that cannot be measured noninvasively.

In intraindividual amplitude changes the congenital differences between different individuals, like for instance differences in skeletal dimensions and possible differences in the conduction system of the heart, play practically no role. However, there is variability also in intraindividual amplitude changes.

Intraindividual variability is a hindrance in serial ECG analysis, where ECG's of the same individual, but taken at different times, are compared. Two sources of intraindividual variability can be distinguished as follows: variability related to the technical circumstances during ECG recording and non-pathologic biologic variability. Among the technical sources, variation in electrode positioning between recordings is the most confusing (Schijvenaars et al. 2008). According to Shijvenaars the most important biological sources are age and weight.

In addition to the conductivity of thoracic tissues between the heart and the body surface the magnitude of the electrical potential generated by the heart, measured on the thoracic surface, is dependent on the solid angle of the contour of the heart seen from the measurement point on the subjects thoracic surface (Oosterom et al 2000). The magnitude of the solid angle is dependent both on the square of the distance between the measurement point on the thoracic surface and the heart mass, and the area of the contour of the heart mass seen from the measurement point on the body surface (Oosterom et al. 2000).

In addition to the distance between the heart and the thoracic surface, the position of the heart within the thorax virtually determines the electrical force generated by the heart as measured on the thoracic surface. The position of the heart within the thorax is such, that the contour of the left ventricle resembles an asymmetrical ellipsoid, as seen from the anterolateral thoracic surface. The heart can be rotated around its length axis clockwise or counterclockwise. The more the heart rotates clockwise, the shorter. Vice versa, the longer is the transverse axis of the ellipsoid contour of the left ventricle in case the heart rotates counterclockwise. Because the longer axis of the ellipsoid stays the same, the surface area of the ellipsoid is directly related to the length of the shorter axis. The magnitude of the solid angle seen from the anterolateral surface of the thorax is the greater the more counterclockwise the heart rotates, and the smaller the more the heart rotates clockwise. This phenomenon makes the amplitudes measured on the anterolateral thoracic surface greater, when the heart is counterclockwise rotated and smaller, when the heart is clockwise rotated.

The electrical axis of the heart on the horizontal plane, which is called transitional zone, is defined to be, when in precordial ECG leads V1-V6 the amplitudes of R and S waves in the same QRS complex are equal. Traditionally the axis is considered to be normal, if the transition zone is between the leads V3 and V4, when in practice the S wave is more prominent than the R wave in the lead V3, and the R wave is more prominent than the S wave in the lead V4. If the transition zone is more to right, the situation is called counterclockwise rotation, and more to the left the situation is called clockwise rotation.

In 1951 Fowler et al. represented the clockwise and counterclockwise rotation of the heart around its long axis using x-ray angiocardiogram. In 1991 Tahara et al. studied the relationship between shift of the transitional zone on the standard 12-lead ECG and anatomical rotation of the heart in horizontal plane by cardiac computed tomography. In more recent studies the frequency of counterclockwise rotation, no rotation and clockwise rotation has been investigated (Bradford et al 2014, Patel et al. 2017 and Prineas et al. 2018).

The most usual reason for intraindividual changes in the distance between the measuring electrode on the thoracic surface and the heart is the presently usual obesity. The more the distance increases, the more the measured amplitude decreases and vice versa.

In many investigations on the effect of obesity for precordial ECG amplitudes body mass index (BMI) has been found to decrease anterolateral precordial ECG amplitudes (Okin et al. 2000, Abacherli et al. 2009, Kurisu et al. 2015) and cause lateral displacement of the anatomical left ventricular axis (Rider et al. 2016).)

Especially, in serial measurements for follow-up studies, accurate and reproducible amplitude measurements are necessary. There is no common method in use for amplitude correction in follow-up studies. Therefore, there is a need in the art for a method and device for adjusting changes in precordial ECG amplitudes caused by intraindividual changes in solid angle of the heart seen from a point of thoracic surface of the subject.

The present inventors are not aware of prior art disclosing a fast, easy to use and low-cost method and device, aiming for an adjustment of long term intraindividual precordial amplitude changes, in particular for a combination in changes of heart rotation and changes in BMI.

BRIEF DESCRIPTION OF THE INVENTION

An object of the invention is to develop non-invasive methods and devices for adjustment of long term intraindividual changes in precordial ECG amplitudes.

The objects of the invention are achieved by the methods, apparatus, computer software program and the device as characterized in the independent claims. The inventors surprisingly found that it is possible to make percentage corrections in intraindividual subject's amplitude measurements. The amplitude measurements are corrected first, and the corrected amplitudes can then be compared as usually. The preferred embodiments of the invention are disclosed in the dependent claims. Aspects of the invention include methods and a device according to the respective independent claims.

The invention is based on modified solid angle theory. Specifically, the methods disclosed herein introduce corrections for the solid angle of the left ventricle of the heart seen from the measuring electrode on the subject's thoracic surface. Said solid angle is determined by (i) the distance from the measuring electrode to the equivalent dipole of the heart (Oosterom et al 2000), (surrogate in the present method: intraindividual BMI), and (ii) the surface area of the left ventricle seen from the measuring electrode. This surface area is dependent on the angle between the surface of the left ventricle and the measuring electrode. The angle is dependent on the rotation position of the heart around its long axis. As a approximate surrogate for the rotation position has in the present invention been used the angle deviation of the position of the transition zone from the normal rotation area on the horizontal ECG plane.

In sum, the methods disclosed herein may be advantageously used for cost effective comparison of serial, intraindividual precordial ECG amplitudes in long term follow-up. The unifying concept of the methods of the present disclosure and the device is that it introduces corrections for the solid angle of the left ventricle of the heart seen from the measuring electrode on the subjects thoracic surface based on (i) the subject's BMI (the distance from the measuring electrode to the equivalent dipole of the heart), and (ii) the position of the subject's transition zone, which is a measure of the rotation position of the heart and thus of the surface area of the left ventricle seen from the measuring electrode.

As noted above, the effect of the heart mass subtended seen from the exploring electrode on the thoracic surface is determined by the angle deviation of the transitional zone of ECG from the no rotation area on the horizontal plane (see (ii) above). Because the degree of the angle deviation between two adjoining electrodes for the leads V2, V3, V4, V5 and V6 is about 20 degrees, the corresponding percentage adjustment is defined to be 20%. If the transitional zone is located between two electrodes, the degree of the angle deviation is defined to be 10%. The adjustment is decreasing in counterclockwise rotation and increasing in clockwise rotation. In light of the foregoing, provided is a method of determining a subject's corrected precordial ECG amplitude in an ECG measurement, comprising the steps of (a) providing said subject's ECG data obtained from a first ECG measurement made at a first time point in paper form or stored on a memory device, wherein said ECG was recorded using a standardized and reproducible electrode placement method, and wherein said ECG data comprises data for a six lead V1-V6 precordial ECG;

(b) providing said subject's ECG data obtained from a second ECG measurement made at a second time point, which is after the first time point in paper form or stored on a memory device, wherein said ECG was recorded using a standardized and reproducible electrode placement method, and wherein said ECG data comprises data for a six lead V1-V6 precordial ECG and a precordial ECG amplitude A; and (c) determining a percentage correction value R by determining the position of the transition zone in said data of a six lead V1-V6 precordial ECG from said first ECG measurement in paper form or stored on a memory device and assigning to it a percentage correlation value R1, and determining the position of the transition zone in said data of a six lead V1-V6 precordial ECG from said second ECG measurement in paper form or stored on a memory device and assigning to it a percentage correlation value R2, wherein R1 or R2 is independently (i) about −30% in case the transition zone is between lead V1 and lead V2, (ii) about −20% in case the transition zone is around lead V2, (iii) about −10% in case the transition zone is between lead V2 and lead V3, (iv) about 0 in case the transition zone is around lead V3 or between lead V3 and lead V4, (v) about 10% in case the transition zone is around lead V4, (vi) about 20% in case the transition zone is between lead V4 and lead V5, (vii) about 30% in case the transition zone is around lead V5, and (viii) about 40% in case the transition zone is between lead V5 and lead V6;

and calculating the percentage correction value R using formula (1)

$$R = R2 - R1; \text{ and} \tag{1}$$

(d) calculating a subject's corrected precordial ECG amplitude A* from a precordial ECG amplitude value A from said ECG measurement from said second time point, and the percentage correction value R, using formula (2)

$$A^* = A + (R \times A); \tag{2}$$

5 thereby determining a subject's corrected precordial ECG amplitude in an ECG measurement, and providing said subject's corrected precordial ECG amplitude in an ECG measurement in paper form or via a display. In the prior art, the correction of the amplitude value has been made grounded on the observations that obese subjects have lower precordial antero-lateral amplitudes, by simply multiplying the amplitude value by the BMI value. These BMI values are interindividual and dependent both on the weight and height of the subject.

In contrast, in the method of the present disclosure the weight of the BMI value of this individual with his/her individual height it is converted to correspond to the weight of the "ideal" BMI value 23. The decreasing or increasing difference between the actual and the "ideal" weight determines the percentage correction for the measured amplitude according the method of the present disclosure. These changes are intraindividual and only the weight changes.

Hence, the method is especially useful in the long-term follow-up of individual human subjects which undergo weight changes. In such measurements comprising the measurement of precordial ECG amplitudes, the effect of said change in distance is determined by the change in BMI. Because the gain in weight is lifting the diaphragm to a more transverse position, the anterolateral precordial amplitudes decrease. Therefore, a simple distance, instead the square of the distance between the equivalent dipole of the heart and the thoracic surface is used, thus deviating from the original solid angle theory. The adjustment was found to be 5% for two units of BMI, decreasing under BMI value of 23 and increasing over that value. In accordance with correction factor (ii) explained above, further provided is a method of determining a subject's corrected precordial ECG amplitude from an ECG measurement, comprising the steps of (a) providing a first BMI value of a subject, wherein said first BMI value is obtained or obtainable from a first time point;

(b) providing a second BMI value of said subject, wherein said second BMI value is obtained or obtainable from a second time point of an ECG measurement, which is after said first time point;

(c) providing said subject's ECG data in paper form or stored on a memory device obtained from said ECG measurement made at said second time point, wherein said ECG was recorded using a standardized and reproducible electrode placement method, and wherein said ECG data comprises data for a precordial ECG amplitude A;

(d) determining a percentage correction value B by assigning said first BMI value a first percentage correction value B1, and said second BMI value a second percentage correction value B2, wherein B1 and B2 are independently assigned a percentage correction value according to the following table

| BMI | B1 or B2 in % |
|---|---|
| 17 or 18 | −15 |
| 19 or 20 | −10 |
| 21 or 22 | −5 |
| 23 | 0 |
| 24 or 25 | 5 |
| 26 or 27 | 10 |
| 28 or 29 | 15 |
| 30 or 31 | 20 |

6

-continued

| BMI | B1 or B2 in % |
|---|---|
| 32 or 33 | 25 |
| 34 or 35 | 30 |
| 36 or 37 | 35 |
| 38 or 39 | 40 |
| 40 or 41 | 45 |
| 42 or 43 | 50 |
| 44 or 45 | 55 |
| 46 or 47 | 60 |
| 48 or 49 | 65 |
| 50 or 51 | 70, | and calculating the percentage correction value B using formula (3)

$$B = B2 - B1; \text{ and} \tag{3}$$

(e) calculating a subject's corrected precordial ECG amplitude A* from said precordial ECG amplitude value A from said ECG measurement, and said percentage correction value B, using formula (4)

$$A^* = A + (B \times A); \tag{4}$$

thereby determining a subject's corrected precordial ECG amplitude from an ECG measurement, and providing said subject's corrected precordial ECG amplitude in an ECG measurement in paper form or via a display.

While amplitude measurements can be corrected for either one of the above, preferably the amplitude measurements are corrected for both (i) and (ii). Hence, advantageously the two foregoing methods can be combined, wherein the sum of both percentage correction values gives the final percentage correction. Hence, further provided is a method of determining a subject's corrected precordial ECG amplitude from an ECG measurement, comprising the steps of (a) providing a first BMI value of a subject, wherein said first BMI value is obtained from a first time point of a first ECG measurement;

(b) providing a second BMI value of said subject, wherein said second BMI value is obtained from a second time point of a second ECG measurement which is after said first time point;

(c) providing said subject's ECG data in paper form or stored on a memory device obtained from said first ECG measurement, wherein said ECG was recorded using a standardized and reproducible electrode placement method, and wherein said ECG data comprises data for a six lead V1-V6 precordial ECG;

(d) providing said subject's ECG data in paper form or stored on a memory device obtained from said second ECG measurement, wherein said ECG was recorded using a standardized and reproducible electrode placement method, and wherein said ECG data comprises data for a six lead V1-V6 precordial ECG and a precordial ECG amplitude A;

(e) determining a first percentage correction value B by assigning said first BMI value a first percentage correction value B1, and said second BMI value a second percentage correction value B2, wherein B1 and B2 are independently assigned according the following table

| BMI | B1 or B2 in % |
|---|---|
| 17 or 18 | −15 |
| 19 or 20 | −10 |
| 21 or 22 | −5 |
| 23 | 0 |
| 24 or 25 | 5 |
| 26 or 27 | 10 |
| 28 or 29 | 15 |
| 30 or 31 | 20 |
| 32 or 33 | 25 |
| 34 or 35 | 30 |
| 36 or 37 | 35 |
| 38 or 39 | 40 |
| 40 or 41 | 45 |
| 42 or 43 | 50 |
| 44 or 45 | 55 |
| 46 or 47 | 60 |
| 48 or 49 | 65 |
| 50 or 51 | 70 | and calculating the absolute value using formula (3)

$$B = B2 - B1; \text{ and} \tag{3}$$

(f) determining a second percentage correction value R by determining the position of the transition zone in said data of a six lead V1-V6 precordial ECG from said first ECG measurement and assigning to it a percentage correlation value R1, and determining the position of the transition zone in said data of a six lead V1-V6 precordial ECG from said second ECG measurement and assigning to it a percentage correlation value R2, wherein R1 or R2 is independently (i) about −30% in case the transition zone is between lead V1 and lead V2, (ii) about −20% in case the transition zone is around lead V2, (iii) about −10% in case the transition zone is between lead V2 and lead V3, (iv) about 0 in case the transition zone is around lead V3 or between lead V3 and lead V4, (v) about 10% in case the transition zone is around lead V4, (vi) about 20% in case the transition zone is between lead V4 and lead V5, (vii) about 30% in case the transition zone is around lead V5, and (viii) about 40% in case the transition zone is between lead V5 and lead V6;

and calculating the percentage correction value R using formula (1)

$$R = R2 - R1; \text{ and} \tag{1}$$

(g) calculating a subject's corrected precordial ECG amplitude A* from a precordial ECG amplitude value A from said second ECG measurement using formula (5)

$$A^* = A + [(B \times R) \times A]; \tag{5}$$

thereby determining a subject's corrected precordial ECG amplitude in an ECG measurement, and providing said subject's corrected precordial ECG amplitude in an ECG measurement in paper form or stored on a memory device. The present disclosure also provides a device (1), which is suitable for use in a method as defined herein above, wherein the device suitable for use in a method according to the present disclosure, wherein said device comprises (a) an alignment (2) of BMI values and a first percentage correction value according the following table

| BMI | |
|---|---|
| 17 or 18 | −15 |
| 19 or 20 | −10 |
| 21 or 22 | −5 |
| 23 | 0 |
| 24 or 25 | 5 |
| 26 or 27 | 10 |
| 28 or 29 | 15 |
| 30 or 31 | 20 |
| 32 or 33 | 25 |
| 34 or 35 | 30 |
| 36 or 37 | 35 |
| 38 or 39 | 40 |
| 40 or 41 | 45 |
| 42 or 43 | 50 |
| 44 or 45 | 55 |
| 46 or 47 | 60 |
| 48 or 49 | 65 |
| 50 or 51 | 70 |

(b) illustrations (3) of the form of the respective QRS complex of the transitional zone at different positions of a six lead V1-V6 precordial ECG horizontal plane; and indications (4) of said position of the transitional zone shown in (a) relative to precordial leads V1-V6;

(c) an alignment of said indications (4) of said position of (b) with a corresponding second percentage correction value (5), wherein said alignment indicates one or more of the following (i) to (ix):

| | | |
|---|---|---|
| (i) | −30 | V1-V2 |
| (ii) | −20 | V2 |
| (iii) | −10 | V2-V3 |
| (iv) | 0 | V3 |
| (v) | 0 | V3-V4 |
| (vi) | 10 | V4 |
| (vii) | 20 | V4-V5 |
| (viii) | 30 | V5 |
| (ix) | 40 | V5-V6; | preferably wherein said alignment indicates all of (i) to (ix).

The device (1) of the present disclosure can be used for determining a subject's corrected precordial ECG amplitude in an ECG measurement, wherein said use comprises comparing the illustrations of said device of the respective QRS complex of the transitional zone at different positions of a six lead precordial ECG horizontal plane as disclosed herein above with the QRS complexes of a six lead V1-V6 precordial ECG measurement of said subject provided in paper form or stored on a memory device, such as to determine the position of the transitional zone in said six lead precordial ECG measurement, and conducting the method of the present disclosure.

Consequently, the device of the present disclosure can be used for improving the accuracy of electrocardiographic methods depending on precordial ECG amplitude measurements; wherein said use comprises conducting the method(s) of the present disclosure.

Moreover, the present disclosure provides an apparatus (601) for determining a subject's corrected precordial ECG amplitude in an ECG measurement, comprising:

at least one processor (620), and at least one memory (630) for storing instructions (631) to be executed by the at least one processor (620), wherein the at least one memory (630) and the instructions are configured to, with the at least one processor (620), cause the apparatus (601) at least to perform:

maintaining (301), in said at least one memory, said subject's ECG data obtained from a first ECG measurement made at a first time point, wherein said ECG was recorded using a standardized and reproducible electrode placement method, and wherein said ECG data comprises data for a six lead V1-V6 precordial ECG;

maintaining (302), in said at least one memory, said subject's ECG data obtained from a second ECG measurement made at a second time point, which is after the first time point, wherein said ECG was recorded using a standardized and reproducible electrode placement method, and wherein said ECG data comprises data for a six lead V1-V6 precordial ECG and a precordial ECG amplitude A;

determining (303) a percentage correction value R by determining the position of the transition zone in said data of a six lead V1-V6 precordial ECG from said first ECG measurement and assigning (303) to it a percentage correlation value R1, and determining (303) the position of the transition zone in said data of a six lead V1-V6 precordial ECG from said second ECG measurement and assigning (303) to it a percentage correlation value R2, wherein R1 or R2 is independently (i) about −30% in case the transition zone is between lead V1 and lead V2, (ii) about −20% in case the transition zone is around lead V2, (iii) about −10% in case the transition zone is between lead V2 and lead V3, (iv) about 0 in case the transition zone is around lead V3 or between lead V3 and lead V4, (v) about 10% in case the transition zone is around lead V4, (vi) about 20% in case the transition zone is between lead V4 and lead V5, (vii) about 30% in case the transition zone is around lead V5, and (viii) about 40% in case the transition zone is between lead V5 and lead V6;

and calculating (303) the percentage correction value R using formula (1)

$$R = R2 - R1; \text{ and} \tag{1}$$

calculating (304) a subject's corrected precordial ECG amplitude A* from a precordial ECG amplitude value A from said ECG measurement from said second time point, and the percentage correction value R, using formula (2)

$$A^{*} = A + (R \times A); \tag{2}$$

thereby determining said subject's corrected precordial ECG amplitude in the ECG measurement; and outputting (305) said subject's corrected precordial ECG amplitude.

Likewise, also provided is a computer program product, embodied on a non-transitory computer readable medium, comprising program instructions, that when run is adapted to determine a subject's corrected precordial ECG amplitude in an ECG measurement by performing:

maintaining (301), in said at least one memory, said subject's ECG data obtained from a first ECG measurement made at a first time point, wherein said ECG data was recorded using a standardized and reproducible electrode placement method, and wherein said ECG data comprises data for a six lead V1-V6 precordial ECG;

maintaining (302), in said at least one memory, said subject's ECG data obtained from a second ECG measurement made at a second time point, which is after the first time point, wherein said ECG was recorded using a standardized and reproducible electrode placement method, and wherein said ECG data comprises data for a six lead V1-V6 precordial ECG and a precordial ECG amplitude A;

determining (303) a percentage correction value R by determining the position of the transition zone in said data of a six lead V1-V6 precordial ECG from said first ECG measurement and assigning (303) to it a percentage correlation value R1, and determining (303) the position of the transition zone in said data of a six lead V1-V6 precordial ECG from said second ECG measurement and assigning (303) to it a percentage correlation value R2, wherein R1 or R2 is independently (i) about −30% in case the transition zone is between lead V1 and lead V2, (ii) about −20% in case the transition zone is around lead V2, (iii) about −10% in case the transition zone is between lead V2 and lead V3, (iv) about 0 in case the transition zone is around lead V3 or between lead V3 and lead V4, (v) about 10% in case the transition zone is around lead V4, (vi) about 20% in case the transition zone is between lead V4 and lead V5, (vii) about 30% in case the transition zone is around lead V5, and (viii) about 40% in case the transition zone is between lead V5 and lead V6;

and calculating (303) the percentage correction value R using formula (1)

$$R = R2 - R1; \text{ and} \tag{1}$$

calculating (304) a subject's corrected precordial ECG amplitude A* from a precordial ECG amplitude value A from said ECG measurement from said second time point, and the percentage correction value R, using formula (2)

$$A^{*} = A + (R \times A); \tag{2}$$

thereby determining said subject's corrected precordial ECG amplitude in the ECG measurement; and causing (305) outputting said subject's corrected precordial ECG amplitude.

The present invention provides a fast and easy way for cost effective comparison of serial, intraindividual precordial ECG amplitudes in long term follow-up. The method and device can be employed all over the world, anywhere the recording of ECG is possible. No extra devices or even electricity is needed. The invention improves remarkably the accuracy of long-term follow-up of, for instance, heart left ventricular hypertrophy and hypertension.

Accordingly, further provided is a method of diagnosing left ventricular hypertrophy and/or hypertension in a subject, and a use of the device of the present disclosure for diagnosing left ventricular hypertrophy and/or hypertension in a subject, as further defined in the claims.

If the placement of precordial ECG amplitudes is standardized and reproduced satisfactory, also the ageing of cardiovascular system and the development of prehypertension in an individual human subject can be followed.

BRIEF DESCRIPTION OF THE DRAWINGS

In the following, the invention will be described in greater detail by means of preferred embodiments with reference to the accompanying drawings.

FIGS. 3 to 5 illustrate processes according to embodiments.

DETAILED DESCRIPTION OF THE INVENTION

Figure 1:
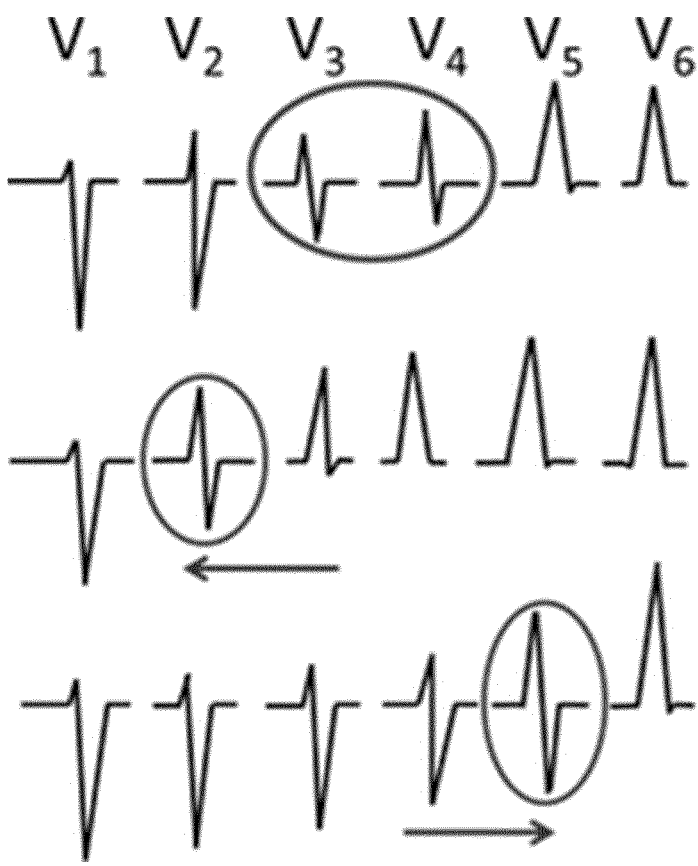
FIG. 1 illustrates the prior art understanding of rotation of the QRS transitional zone, which is FIG. 1 of Patel et al. (2017). As illustrated in this figure, in the prior art the situation is considered as no rotation, if the transition zone is between leads V3 and V4 (top panel). If the transition occurs at or before V2, this is traditionally called counterclockwise rotation (middle panel). If the transition occurs after V4, this is traditionally called clockwise rotation (bottom panel).

In order to find a solution to the need of adjusting the precordial ECG amplitudes to the changes in the surface area of the contour of the left ventricular mass of the heart seen from the anterolateral thoracic surface, the present inventors examined changes in the position of the transitional zone on the horizontal plane of ECG as found in the literature.

Normally the R wave amplitude increases from V1 to V5. Around V3 or V4 the R waves become larger than the S waves and this is called the 'transitional zone'. In the prior art, the situation is considered as no rotation, if the transition zone is between leads V3 and V4 (see FIG. 1 top panel). If the transition occurs at or before V2, this is traditionally called counterclockwise rotation (See FIG. 1 middle panel). If the transition occurs after V4, this is traditionally called clockwise rotation (see FIG. 1 bottom panel). In the present invention, the definition of no rotation, clockwise rotation and counter-clockwise rotation is modified on the basis of the following reasons.

In 1951, Fowler et al. studied 34 patients by electrocardiography for electrical position of the heart, and by x-ray and angiogram for anatomic position of the heart. A significant association between electrocardiographic and anatomic positions of the heart was found in rotation around the longitudinal axis. In 1991, Tahara et al. studied 102 subjects using computed tomography. Counterclockwise rotation (CCWR) was found in 41 subjects, normal rotation (NR) in 31 subjects and clockwise rotation (CWR) in 30 subjects. The mechanism of CCWR and CWR could be attributed to the septal angle in about two-thirds of the cases (27/41 in CCWR and 24/30 in CWR). Left septal fascicular block was suspected to be responsible for CCWR in the 14 patients. Nakamura et al 2012 found in 9067 subjects 35.8% in CCWR, 56% in NR and 8.2% in CWR. There was a significant positive association of clockwise rotation and a significant inverse association of counterclockwise rotation with CVD mortality in men as well as in men and women combined, independent of confounding factors including other ECG changes.

Bradford et al. (2014) studied 5541 adults without cardiovascular diseases (CVD) or any major electrocardiogram abnormalities. At baseline, 3500 participants had counterclockwise rotation, 1759 normal rotation and 282 clockwise rotation. During a median follow of 14.6 years clockwise rotation was significantly associated with increased risk of all-cause mortality and CVD mortality. In contrast, counterclockwise rotation was associated with significantly lower risk of all-cause mortality and non-significant association with CVD mortality.

Among 13567 study participants aged 45 to 64 years, Patel et al. (2017) studied key correlates of changes in the status of clockwise and counterclockwise rotation over time as well as the association of rotation status with incidence of coronary heart disease, stroke, composite CVD, CVD deaths and non-CVD deaths over 23 years of follow-up. At baseline, counterclockwise rotation was most prevalent (52.9%), followed by normal rotation (40.5%) and clockwise (6.6%) rotation. Of patients with no rotation at baseline, 42.1% remained in the no rotation group over 9 years, and 57.2% experienced either counterclockwise rotation (46.2%) or clockwise rotation (11.1%) during follow-up visits. Only 0.6% experienced both counterclockwise and clockwise rotations. Among participants with counterclockwise rotation at baseline, 72.5% stayed in the same rotation category over 9 years, and 26.7% showed no rotation at some visits. Only 0.8% of those with a counterclockwise rotation at baseline experienced clockwise rotation over 9 years. Among individuals with clockwise rotation at baseline, 33.2% stayed in the same rotation category over 9 years, but 58.4% experienced normal rotation and 8.4% had counterclockwise rotation during follow-up. Clockwise rotation was significantly associated with higher risk of heart failure and non-CVD death. Counterclockwise rotation, the most prevalent QRS transition zone pattern, demonstrated the lowest risk of CVD and mortality, whereas clockwise rotation was associated with the most high risk of heart failure and non-CVD mortality.

Prineas et al. (2018) examined the distributions of normal, clockwise (CW) and counterclockwise (CCW) QRS transition zones in 4624 black and white men and women free of cardiovascular disease and any major abnormalities. CW transition zones were least observed (6.2%) and CCW were most prevalent (60.1%) with normal in an intermediate position (33.7%). Compared to normal group were the people in CW group older and more obese.

The latest three examinations are estimated the most reliable, because standardized methods were used in the placement of precordial electrodes. In these studies, the subjects with cardiovascular diseases or any major electrocardiogram abnormalities were excluded. The mean of the subjects with counterclockwise rotation in the three studies was 58.7%, normal rotation 35.3% and clockwise rotation 6.0%. Because of the great number of counterclockwise rotation, in apparently healthy people, the authors questioned the definition of normal rotation. The great variability of rotation groups during the follow-up emphasizes the need for adjusting the intra-individual precordial ECG amplitude measurements during a long-term follow-up.

In the light of the foregoing information, and in deviation to the prior art as shown in FIG. 1, the definition of the normal rotation in the method of the present invention contain the situation, when the transition zone is also at lead V3. In that way transition zone right from V3 is defined herein below as counterclockwise and from the lead V4 and left from it, clockwise.

According the above mentioned principles, compared to the no-rotation, the angle and the area of the asymmetrical ellipsoid between the electrodes for the leads V3 and V2 is about 10%, at the electrode for the lead V2 it is about 20%, and between the electrodes for the leads V1 and V2 about 30% greater. Correspondingly, at the electrode for the lead V4 the angle and the area of the ellipse is about 10%, between the electrodes for the leads V4 and V5 about 20%, at the electrode for the lead V5 about 30%, and between the electrodes for the leads V5 and V6 about 40% smaller.

When considering the above presented principle, the amplitude measured between the electrodes V3 and V2 is about 10% greater than in the normal rotation area, and correspondingly about 20% greater at the electrode V2, and about 30% greater between the electrodes V1 and V2. Correspondingly, the amplitude is at the electrode V4 about 10% smaller, between the electrodes V4 and V5 about 20% smaller, at the electrode V5 about 30% smaller, and between the electrodes V5 and V6 about 40% smaller than in the normal rotation area. Thus, for comparison of intraindividual precordial ECG amplitude changes, the measured amplitudes must be corrected by the measured percentages according to the horizontal rotation decreasing in counterclockwise rotation and increasing in clockwise rotation.

The term "about" as used herein is intended to mean±2%, preferably ±1%, more preferably ±0.5%, even more preferably ±0.2%, and most preferably ±0.1%. For example, "about 10%" is intended to mean 10±2%, preferably 10±1%, more preferably 10±0.5%, even more preferably 10±0.2%, and most preferably ±0.1%.

The precondition for the successful use of the present method is a standardized and reproducible placement of precordial ECG electrodes. If electrode placement is not standardized and reproducible, the position of the electrode change, which affects both factors of the solid angle. Suitable methods and devices for a standardized and reproducible placement of precordial ECG electrodes are disclosed, for example, in FI20196062, the disclosure of which is incorporated herein in its entirety. Specifically, the precordial electrodes can be placed by (i) determining the horizontal level of the electrodes for leads V4, V5 and V6, wherein the horizontal level is determined to be between (0.088×body height) [cm] and (0.092×body height) [cm] downwards from the sternal notch along the sternal midline;

(ii) placing the electrode for lead V1 from 2.8 cm to 3 cm above the horizontal level along the sternal midline, and from 2.9 cm to 3.5 cm to the subject's right from the sternal midline;

(iii) placing the electrode for lead V2 from 2.8 cm to 3 cm above the horizontal level along the sternal midline, and from 2.9 cm to 3.5 cm to the subject's left of the sternal midline;

(iv) placing the electrode for lead V4 at the horizontal level and (body height/16)±1 [cm] to the subject's left from the sternal midline along the surface of the thorax;

(v) placing the electrode for lead V3 from (0.023×body height) [cm] to (0.025×body height) [cm] from the position of the electrode for lead V2 to the direction of the position for the electrode for lead V4 along the connecting line formed by the position of the electrode for lead V2 and the position of the electrode for lead V4;

(vi) placing the electrode for lead V5 at the horizontal level and ((3×body height)/32)±1 [cm] to the subject's left from the sternal midline along the surface of the thorax; and (vii) placing the electrode for lead V6 at the horizontal and (body height/8)±1 [cm] to the subject's left from the sternal midline along the surface of the thorax.

See also FIG. 1 of WO 2021/110937. Advantageously, the device disclosed in WO 2021/110937 can be used for placing the electrodes as described above and in WO 2021/110937.

For the method of the present invention the electrode for the lead V6 is supposed to be straight to left from the left ventricle of the heart, and the electrode for the lead V2 straight forward from the left ventricle projised on the horizontal plane of the electrodes V4, V5 and V6. The electrode for the lead V4 is supposed to be about at the half-point between the electrodes V2 and V6 on the same horizontal plane. The electrode for the lead V3 as projised at the same horizontal level than the electrodes V4, V5 and V6 is estimated to be at the half-point between the electrodes V2 and V3, and the electrode for the lead V5 is at the half-point between the electrodes V4 and V6 at the same horizontal level. Thus the angle between each electrode would be 22.5 degrees. However, for practical reasons an angle of 20 degrees is used in the method.

The methods disclosed herein are advantageously used for cost effective comparison of serial, intraindividual precordial ECG amplitudes in long term follow-up. For example, the method is especially useful in the long-term follow-up of individual human subjects which undergo weight changes.

Using the above modified definition of normal, clockwise and counterclockwise rotation, and applying the above-explained scientific reasoning, the present inventors provide a method of determining a subject's corrected precordial ECG amplitude from an ECG measurement, comprising the steps of (a) providing said subject's ECG data obtained or obtainable from a first ECG measurement made at a first time point in paper form or stored on a memory device, wherein said ECG was recorded using a standardized and reproducible electrode placement method, and wherein said ECG data comprises data for a six lead V1-V6 precordial ECG;

(b) providing said subject's ECG data obtained or obtainable from a second ECG measurement made at a second time point in paper form or stored on a memory device, which is after the first time point, wherein said ECG was recorded using a standardized and reproducible electrode placement method, and wherein said ECG data comprises data for a six lead V1-V6 precordial ECG and a precordial ECG amplitude A; and (c) determining a percentage correction value R by determining the position of the transition zone in said data of a six lead V1-V6 precordial ECG from said first ECG measurement in paper form or stored on a memory device and assigning to it a percentage correlation value R1, and determining the position of the transition zone in said data of a six lead V1-V6 precordial ECG from said second ECG measurement in paper form or stored on a memory device and assigning to it a percentage correlation value R2, wherein R1 or R2 is independently (i) about −30% in case the transition zone is between lead V1 and lead V2, (ii) about −20% in case the transition zone is around lead V2, (iii) about −10% in case the transition zone is between lead V2 and lead V3, (iv) about 0 in case the transition zone is around lead V3 or between lead V3 and lead V4, (v) about 10% in case the transition zone is around lead V4, (vi) about 20% in case the transition zone is between lead V4 and lead V5, (vii) about 30% in case the transition zone is around lead V5, and (viii) about 40% in case the transition zone is between lead V5 and lead V6;

and calculating the percentage correction value R using formula (1)

$$R = R2 - R1; \text{ and} \tag{1}$$

(d) calculating a subject's corrected precordial ECG amplitude A* from a precordial ECG amplitude value A from said ECG measurement from said second time point, and the percentage correction value R, using formula (2)

$$A^* = A + (R \times A); \tag{1}$$

thereby determining a subject's corrected precordial ECG amplitude in an ECG measurement, and providing said subject's corrected precordial ECG amplitude in an ECG measurement in paper form or via a display.

According to an embodiment, there is provided a computer-implemented method of determining a subject's corrected precordial ECG amplitude from an ECG measurement as illustrated with the flow chart of FIG. 3. Said method may be carried out fully by a computing device. Said method comprises:

performing, in blocks 301 to 304, the steps of steps (a)-(d) as described in the previous paragraph, respectively; and outputting, in block 305, said subject's corrected precordial ECG amplitude.

The providing steps of blocks 301, 302 may correspond to maintaining the associated information (and optionally also the information based on which said information has been calculated or obtained) in a memory.

The outputting in block 305 may comprise, for example, displaying said subject's corrected precordial ECG amplitude in the ECG measurement to a user via a display comprised in or electrically connected to the apparatus. Additionally or alternatively, the outputting in block 305 may comprise outputting said subject's corrected precordial ECG amplitude in the ECG measurement to a second apparatus for displaying said subject's corrected precordial ECG amplitude in the ECG measurement to a user, where said second apparatus is connected to the apparatus via at least one communication link and/or at least one communication network.

In some embodiments, said subject's corrected precordial ECG amplitude may be stored to a memory.

One measure of whether a subject is under weight, over-weight, or obese is the body mass index (BMI). The BMI is derived from the mass (weight in kg) and height of a person (in metres). Specifically, the BMI is defined as the body mass divided by the square of the body height.

In the context of the present disclosure, the subject is a human subject, preferably an adult human subject, such as a human subject being at least 18, 19, or 20 years old. At this age, a human subject statistically has a normal (healthy) BMI at a value of 23.

The methods disclosed herein improves the accuracy of all electrocardiographic methods depending on precordial amplitude measurements. The determination of a correct ECG amplitude is of high diagnostic relevance. The herein disclosed correction can be applied to all precordial amplitude measurements, like P wave, Q wave, R wave, S wave, ST line, T wave and U wave.

Merely one example for illustration is the Sokolow Lyon index. The diagnostic method using this index was published in 1949 by Sokolow and Lyon. The Sokolow-Lyon index is used in the diagnosis of left ventricular hypertrophy (LVH), which is characterized by a thickening of the heart muscle of the left ventricle of the heart. The Sokolow-Lyon index is calculated by the sum of the amplitude of the S wave in the V1 lead and of the amplitude of the R wave in the V5 or V6 lead (whichever is larger). A sum of more than 3.5 mV (or more than 35 mm) is indicative for the presence of left ventricular hypertrophy (LVH). The mean BMI was 20 in 1949, when the Sokolow-Lyon index was expressed, and at the present the mean BMI is about 27, which has not been noticed in the common prior art.

In the investigations of Okin et al. (2000), Abacherli et al. 2009) and Kurisy et al. (2015) the patients were classified into four groups according the body mass index (BMI): underweight (<18.5 kg/m×m), normal weight (18.5-24.9 kg/m×m) overweight (25-29.9 kg/m×m) and obese (=1>30 kg/m×m). With increasing BMI, QRS axis shifted rightward to leftward and R-wave heights in leads V4-V5 were significantly lower paradoxically in the obese than the other groups. Also, with increasing BMI, Sokolow-Lyon index corrected by left ventricular mass (LVM) decreased progressively.

In the study of Hassing et al. (2019) increased BMI was related with decreased Sokolow-Lyon voltage on a standard twelve lead electrocardiogram in healthy young individuals also in the range of normal MBI (18.5-24.9).

Cuspidi et al (2016) found that Sokolow-Lyon voltage multiplied by BMI improved the correlation between voltage and echographically determined left ventricular hypertrophy. Snelder et al. (2020) corrected Sokolow-Lyon index for BMI. They expressed a limit value of 885 mm×kg/m×m for electrocardiographic left ventricular hypertrophy. A more complicated algorithm between echocardiographic left ventricular hypertrophy (LVH) and age, sex, BMI and ECG voltages by Norman et al (1993).

A practical solution to adjust the effects of left axis deviation and BMI to precordial ECG amplitudes in diagnostics of left ventricular hypertrophy was presented by Rider et al. (2016). In their study overall 1295 participants were included, 821 with a wide range of BMI (17.1-53.3 kg/m×m) initially underwent cardiac magnetic resonance evaluation of anatomical left ventricular (LV) axis, LV mass and 12-lead surface ECG in order to generate an adjustment factor applied to the Sokolow-Lyon criteria. This factor was then validated in a second cohort (n=520, BMI 15.9-63.2 kg/m×m). When matched for LV mass, the combination of leftward anatomical axis deviation and increased BMI resulted in a reduction of the Sokolow-Lyon index, by 4 mm in overweight and 8 mm in obesity. After adjusting for this in the initial cohort, the sensitivity of the Sokolow-Lyon index increased (overweight: 12.8% to 30.8%, obese: 3.1% to 27.2%) approaching that seen in the normal weight (37.8%). Similar results were achieved in the validation cohort (specificity increased in overweight: 8.3% to 39.1%, obese: 9.4% to 25.0%) again approaching normal weight (39%). Importantly, specificity remained excellent (>93.1%). This study used magnetic resonance imaging, that is more accurate than the echocardiography used in the before mentioned investigations.

Despite the significant improvement in the correlation between precordial ECG amplitudes and left ventricular mass the sensitivity of the ECG remains poor at around 30% in all the referred investigations. Also, individual subjects cannot be defined not more accurate, than belonging to a defined BMI group in most studies.

In all of the above referred investigations in the prior art interindividual variability in ECG amplitudes were considered. One of the greatest differences between intraindividual and interindividual variability is that in intraindividual variability, the differences in body habitus, caused by differences in skeletal dimensions, are negligible in long term follow-up. Besides the technical differences, like for instance variation in electrode positions, the most important differences in intraindividual amplitude variability are soft tissue changes, like obesity and changes in heart position, that also are depending on soft tissue changes. These changes are, at least theoretically, measurable, but the effect of, for instance, possible subclinical conduction disturbances of the heart (Sathananthan et al. 2015) cannot be noninvasively measured currently. Therefore, the possible changes in intraindividual amplitudes are more accurate than the absolute amplitudes. However, because subclinical changes can have an effect also on measurements of intraindividual amplitude changes, the adjustment of amplitude measurements in the present invention is not made more accurate than to the nearest 5%.

Horton et al. (1977) found that Sokolow-Lyon voltage multiplied by the square of echocardiographically measured distance between mid-left ventricle and the chest's wall improve the correlation between voltage and left ventricular mass. The magnitude of the solid angle of the heart is dependent both on the square of the distance between the measurement point on the thoracic surface and the heart mass, and the area of the contour of the heart mass seen from the measurement point on the body surface. Using body surface mapping (BSM), magnetic resonance imaging and the measured geometry of the thorax the individual position of a stationary equivalent current dipole of the heart was computed by Oosterom et al. (2000). For a subject with a mean weight of 75.5 kg and mean height of 177 cm the distance from the point of the electrode for the lead V2 on the thoracic surface to the equivalent dipole was 5.5 cm. This distance was used for computing the effect of the change in weight to the distance between the thoracic surface and the equivalent dipole of the heart in the present invention. Supposing the increase in the distance being 0.5 cm layer of fat tissue, and using the form of Mosteller (1987), for body surface area, the volume (9.5 dl) and the weight (8.55 kg) using the density value of 0.9 were counted. The mean increase in distance was 0.5 cm/5.5 cm=9%. Tafeit et al (2019) found in their study, that the mean thickness of the subcutaneous fat layer on upper back, front chest, lateral chest, upper abdomen, lower abdomen and lower back in men, without any special training, was 9.5 mm. The thickness on the anterior thorax was 7.6 mm and on the lateral thorax 9.8 mm. Because the position of the leads V1-V4 can be classified to be on the anterior thorax and of the leads V5 and V6 on the lateral thorax has the mean thickness on the anterior and lateral thorax counted to be 8.3 mm and the corrected extra thickness of the extra fat layer was counted to be 8.3 mm/9.5 mm×0.5 cm=0.44 cm. So, the percentage increase of the fat layer was 0.44 cm/5.5 cm×100=8.0%. Thus, percentage change of 1 kg in weight is 8%/9.5 dl=0.84%, and percentage change of 1 unit in BMI (about 3 kg) 3×0.84% is 2.52%, rounded 2.5%.

According to the solid angle theory, the square of the distance should be used. However, the gain in weight caused by obesity is lifting the diaphragma and turning the heart to a more transverse position, which decreases at least anterolateral precordial amplitudes. So, using the square of the distance should decrease amplitudes too much. Therefore, the simple magnitude of the distance was used in counting.

On the basis of the aforementioned, a change of 4 units of BMI (12 kg) changes the measured precordial ECG amplitudes by 10%, decreasing the amplitude after gain in weight and increasing the amplitudes after loss in weight. To make the adjustment of the amplitudes easy, and to keep the unit of amplitudes as millivolts, the BMI value 23, which is defined good for health (Fontana and Frank 2014), was chosen for a value for comparison on the ground of BMI changes. So, in the method of the present invention, at the BMI 23 no adjustment for the BMI is needed. At a BMI below the value of 23, the amplitudes are decreased by 5% for every two units in BMI. Above a BMI of 23, the amplitudes are increased by 5% for every two units in BMI.

In sum, as the gain in weight is lifting the diaphragm to a more transverse position, the anterolateral precordial amplitudes decrease. Therefore, a simple distance, instead the square of the distance between the equivalent dipole of the heart and the thoracic surface is used, thus deviating from the original solid angle theory. The adjustment was found to be 5% for two units of BMI, decreasing under BMI value of 23 and increasing over that value.

In view of the foregoing, provided is a method of determining a subject's corrected precordial ECG amplitude from an ECG measurement, comprising the steps of (a) providing a first BMI value of a subject, wherein said first BMI value is obtained or obtainable from a first time point;

(b) providing a second BMI value of said subject, wherein said second BMI value is obtained or obtainable from a second time point of an ECG measurement, which is after said first time point;

(c) providing said subject's ECG data in paper form or stored on a memory device obtained or obtainable from said ECG measurement made at said second time point, wherein said ECG was recorded using a standardized and reproducible electrode placement method, and wherein said ECG data comprises data for a precordial ECG amplitude A;

(d) determining a percentage correction value B by assigning said first BMI value a first percentage correction value B1, and said second BMI value a second percentage correction value B2, wherein B1 and B2 are independently assigned a percentage correction value according to the following table

| BMI | B1 or B2 in % |
|---|---|
| 17 or 18 | −15 |
| 19 or 20 | −10 |
| 21 or 22 | −5 |
| 23 | 0 |
| 24 or 25 | 5 |
| 26 or 27 | 10 |
| 28 or 29 | 15 |
| 30 or 31 | 20 |
| 32 or 33 | 25 |
| 34 or 35 | 30 |
| 36 or 37 | 35 |
| 38 or 39 | 40 |
| 40 or 41 | 45 |
| 42 or 43 | 50 |
| 44 or 45 | 55 |
| 46 or 47 | 60 |
| 48 or 49 | 65 |
| 50 or 51 | 70, | and calculating the percentage correction value B using formula (3)

$$B = B2 - B1; \text{ and} \tag{3}$$

(e) calculating a subject's corrected precordial ECG amplitude A* from said precordial ECG amplitude value A from said ECG measurement, and said percentage correction value B, using formula (4)

$$A^* = A + (B \times A); \tag{4}$$

thereby determining a subject's corrected precordial ECG amplitude from an ECG measurement, and providing said subject's corrected precordial ECG amplitude in an ECG measurement in paper form or stored on a memory device.

According to an embodiment, there is provided a computer-implemented method of determining a subject's corrected precordial ECG amplitude from an ECG measurement as illustrated with the flow chart of FIG. 4. Said method may be carried out fully by a computing device. Said method comprises: performing, in blocks 401 to 405, the steps of steps (a)-(e) as described in the previous paragraph, respectively; and outputting, in block 406, said subject's corrected precordial ECG amplitude.

The providing steps of blocks 401 to 403 may correspond here to maintaining the associated information (and optionally also the information based on which said information has been calculated or obtained) in a memory. The outputting in block 406 may be defined as described above in connection with block 305 of FIG. 3.

In some embodiments, said subject's corrected precordial ECG amplitude may be stored to a memory.

Advantageously, both methods can be combined to even further increase the accuracy of a measured ECG amplitude. Accordingly, further provided is a method of determining a subject's corrected precordial ECG amplitude from an ECG measurement, comprising the steps of (a) providing a first BMI value of a subject, wherein said first BMI value is obtained or obtainable from a first time point of a first ECG measurement; (b) providing a second BMI value of said subject, wherein said second BMI value is obtained or obtainable from a second time point of a second ECG measurement which is after said first time point;

(c) providing said subject's ECG data in paper form or stored on a memory device obtained or obtainable from said first ECG measurement, wherein said ECG was recorded using a standardized and reproducible electrode placement method, and wherein said ECG data comprises data for a six lead V1-V6 precordial ECG;

(d) providing said subject's ECG data in paper form or stored on a memory device obtained or obtainable from said second ECG measurement, wherein said ECG was recorded using a standardized and reproducible electrode placement method, and wherein said ECG data comprises data for a six lead V1-V6 precordial ECG and a precordial ECG amplitude A;

(e) determining a first percentage correction value B by assigning said first BMI value a first percentage correction value B1, and said second BMI value a second percentage correction value B2, wherein B1 and B2 are independently assigned according the following table

| BMI | B1 or B2 in % |
|---|---|
| 17 or 18 | −15 |
| 19 or 20 | −10 |
| 21 or 22 | −5 |
| 23 | 0 |
| 24 or 25 | 5 |
| 26 or 27 | 10 |
| 28 or 29 | 15 |
| 30 or 31 | 20 |
| 32 or 33 | 25 |
| 34 or 35 | 30 |
| 36 or 37 | 35 |
| 38 or 39 | 40 |
| 40 or 41 | 45 |
| 42 or 43 | 50 |
| 44 or 45 | 55 |
| 46 or 47 | 60 |
| 48 or 49 | 65 |
| 50 or 51 | 70 | and calculating the absolute value using formula (3)

$$B = B2 - B1; \text{ and} \qquad (3)$$

(f) determining a second percentage correction value R by determining the position of the transition zone in said data of a six lead V1-V6 precordial ECG from said first ECG measurement and assigning to it a percentage correlation value R1, and determining the position of the transition zone in said data of a six lead V1-V6 precordial ECG from said second ECG measurement and assigning to it a percentage correlation value R2, wherein R1 or R2 is independently (i) about −30% in case the transition zone is between lead V1 and lead V2, (ii) about −20% in case the transition zone is around lead V2, (iii) about −10% in case the transition zone is between lead V2 and lead V3, (iv) about 0 in case the transition zone is around lead V3 or between lead V3 and lead V4, (v) about 10% in case the transition zone is around lead V4, (vi) about 20% in case the transition zone is between lead V4 and lead V5, (vii) about 30% in case the transition zone is around lead V5, and (viii) about 40% in case the transition zone is between lead V5 and lead V6;

and calculating the percentage correction value R using formula (1)

$$R = R2 - R1; \text{ and} \qquad (1)$$

(g) calculating a subject's corrected precordial ECG amplitude A* from a precordial ECG amplitude value A from said second ECG measurement using formula (5)

$$A^* = A + [(B + R) \times A]; \qquad (5)$$

thereby determining a subject's corrected precordial ECG amplitude in an ECG measurement, and providing said subject's corrected precordial ECG amplitude in an ECG measurement in paper form or stored on a memory device.

According to an embodiment, there is provided a computer-implemented method of determining a subject's corrected precordial ECG amplitude from an ECG measurement as illustrated with the flow chart of FIG. 5. Said method may be carried out fully by a computing device. Said method comprises:

performing, in blocks 501 to 507, the steps of steps (a)-(g) as described in the previous paragraph, respectively; and outputting, in block 508, said subject's corrected precordial ECG amplitude.

The providing steps of blocks 501 to 504 may correspond here to maintaining the associated information (and optionally also the information based on which said information has been calculated or obtained) in a memory. The outputting in block 508 may be defined, e.g., as described above in connection with block 305 of FIG. 3.

In some embodiments, said subject's corrected precordial ECG amplitude may be stored to a memory.

In embodiments, the first time point is a time point, when an earlier ECG measurement of said subject was made, such that the method allows a accurate monitoring of serial, intraindividual precordial ECG amplitudes in long term follow-up. The long-term changes mean in this connection an opposite to acute changes, that have an effect in minutes or hours like, for instance, acute bleeding. The effect of an acute change returns usually in hours or days. In the present invention the cause of long-term changes in amplitudes are changes in the rotation position of the heart and BMI, that both occur over months or years, but at least in weeks.

Accordingly, in embodiments, the first and the second time point may be at least 2 weeks apart, preferably at least 3 weeks apart, more preferably at least 4 weeks apart, more preferably at least 1 month apart, more preferably at least 2 months apart, more preferably at least 3 months apart, more preferably at least 4 months apart, more preferably at least 5 months apart, more preferably at least 6 months apart, more preferably at least 7 months apart, more preferably at least 8 months apart, more preferably at least 9 months apart, more preferably at least 10 months apart, more preferably at least 11 months apart, more preferably at least 12 months apart, such as more than 18 months apart or more than 24 months apart.

In addition or alternatively, there is no upper time limit for the period between the first and the second time point. In embodiments the first and the second time point may be at most 40 years apart, preferably at most 30 years apart, preferably at most 20 years apart, preferably at most 15 years apart, more preferably at most 10 years apart, more preferably at most 8 years apart, more preferably at most 6 years apart, more preferably at most 4 years apart, more preferably at most 2 years apart, more preferably at most 22 months apart, more preferably at most 20 months apart, more preferably at most 18 months apart, more preferably at most 16 months apart, more preferably at most 14 months apart, more preferably at most 12 months apart, more preferably at most 10 months apart, more preferably at most 8 months apart, more preferably at most 6 months apart, more preferably at most 4 months apart, more preferably at most 2 months apart, such as at most 1 month apart.

In the foregoing, the method has been exemplified for two time points, and/or two ECG measurements, respectively. As noted above, the method allows accurate monitoring of serial, intraindividual precordial ECG amplitudes in long term follow-up. Accordingly, the methods described herein can, of course, also be repeated multiple times, i.e. for at least one further third time point, when a further ECG measurement is made. This opens up two possibilities for comparison or monitoring. In a first option, the change in BMI and/or the change in the transition zone of the measurement made at the at least one further third time point is always determined in comparison to a fixed value. For example, the change in BMI and/or the change in the transition zone at the third time point is compared to the BMI and/or the transition zone at said first time point and the data of said first ECG measurement. In an alternative, second option, the change in BMI and/or the change in the transition zone at the at least one further third time point is compared to the BMI and/or the transition zone of the directly preceding time point and the data of the directly preceding ECG measurement.

In view of the examples provided herein below, in embodiments the ECG amplitude is determined by the sum of the amplitude of the S wave in lead V1 and the amplitude of the R wave in lead V5 or lead V6, whatever amplitude is higher (Sokolow-Lyon index). In this context, also provided is a method of diagnosing left ventricular hypertrophy and/or hypertension in a subject, wherein said method comprises conducting the method as disclosed herein above, wherein a corrected ECG amplitude A* of more than 3.5 mV is indicative of left ventricular hypertrophy and/or hypertension.

Figure 2:
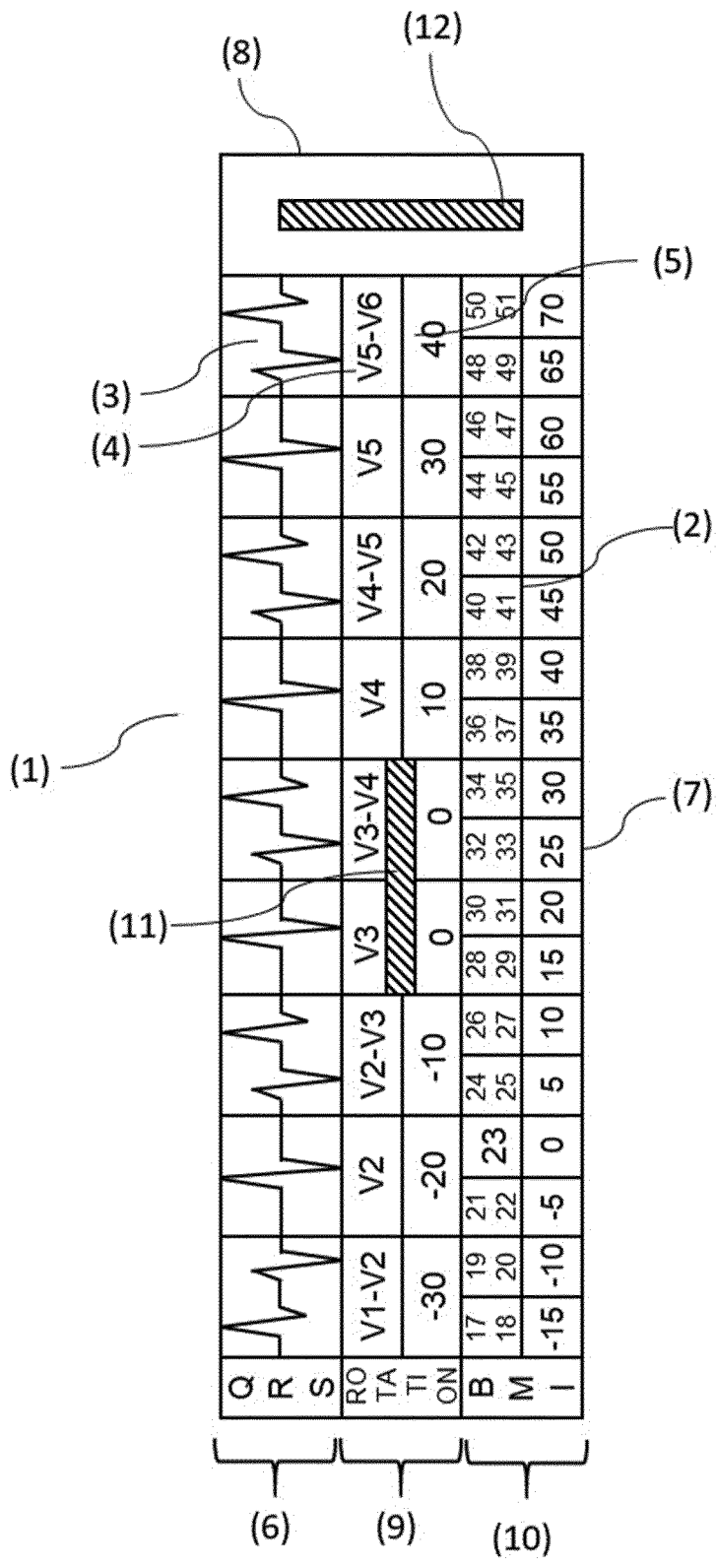
FIG. 2 shows a device (1) of the present disclosure. The device is in a rectangular form having a longer upper and lower side (7), and a shorter left and right side (8). Aligned in three horizontal items (6,9,10), the device shows (i) an alignment (2) of BMI values and a first percentage correction value (10), as further described herein, (ii) illustrations (3) of the form of the respective QRS complex of the transitional zone at different positions of a six lead V1-V6 precordial ECG horizontal plane (6); and indications (4) of said position of the transitional zone relative to precordial leads V1-V6. Said indications (4) of said position are aligned (9) with a corresponding second percentage correction value (5). At least the part of the device showing the illustrations (6) are made of a transparent material. The device may comprise at least one handle (11), preferably on the middle of the device, and optionally at least one further handle (12) on the right side of the device, such as at the right end of the device.

A further aspect of the present application pertains to a device (see FIG. 2), which implements and simplifies the method of the present disclosure as described herein above. The inventors aimed at to develop a non-invasive and easy to use device with an advantageous price. The device is useable all over the world in all circumstances where the ECG can be registered, without the need of any other devices. Hence, the present disclosure further provides a device (1), which is suitable for use in a method as defined herein above, wherein the device is in the form of a rectangular sheet, having an left and right short side (8) and an upper and lower long side (7). Said device (1) comprises an alignment (2) of BMI values and a first percentage correction value according the following table

| BMI | |
| --- | --- |
| 17 or 18 | −15 |
| 19 or 20 | −10 |
| 21 or 22 | −5 |
| 23 | 0 |
| 24 or 25 | 5 |
| 26 or 27 | 10 |
| 28 or 29 | 15 |
| 30 or 31 | 20 |
| 32 or 33 | 25 |
| 34 or 35 | 30 |
| 36 or 37 | 35 |
| 38 or 39 | 40 |
| 40 or 41 | 45 |
| 42 or 43 | 50 |
| 44 or 45 | 55 |
| 46 or 47 | 60 |
| 48 or 49 | 65 |
| 50 or 51 | 70 |

The device (1) further comprises illustrations (3) of the form of the respective QRS complex of the transitional zone at different positions of a six lead V1-V6 precordial ECG horizontal plane; and indications (4) of said position of the transitional zone relative to precordial leads V1-V6.

In addition, the device (1) comprises an alignment of said indications (4) of said position of the transitional zone with a corresponding second percentage correction value (5), wherein said alignment indicates one or more of the following (i) to (ix):

| (i) | −30 | V1-V2 |
| --- | --- | --- |
| (ii) | −20 | V2 |
| (iii) | −10 | V2-V3 |
| (iv) | 0 | V3 |
| (v) | 0 | V3-V4 |
| (vi) | 10 | V4 |
| (vii) | 20 | V4-V5 |
| (viii) | 30 | V5 |
| (ix) | 40 | V5-V6; | preferably wherein said alignment indicates all of (i) to (ix). These illustrations and alignments are preferably aligned in three horizontal items (6,9,10). In embodiments, in the uppermost item (6) is illustrated the form of the QRS complex in different positions of ECG horizontal plane transitional zone. In the middle item (9) are upper the electrodes compared to the different transitional zones and lower the percentage adjustments. In the lowest item (10) are upper two BMI values and lower the comparable percentage adjustment. In the lowest item are upper two values of BMI and lower the comparable percentage correction.

In embodiments, at least the part/the horizontal item (6) of the device showing the illustrations (3) are made of a transparent material. This allows a better comparison of the ECG data with the illustrations (3). In other embodiments, the whole device is basically made of a transparent material. In principle, any suitable transparent material may be used. The device (1) may comprises at least one handle (11), preferably at least one handle on the middle of the device, and optionally at least one further handle (12) on the right side of the device, such as at the right end of the device. The handles allow for easy moving of the device.

The device described herein may be used for determining a subject's corrected precordial ECG amplitude in an ECG measurement. Indeed, the device described herein may be used for improving the accuracy of any sort of electrocardiographic methods depending on precordial ECG amplitude measurements. For example, the device (1) may be used for diagnosing left ventricular hypertrophy and/or hypertension in a subject, as described herein above.

Said uses have in common that they usually comprise the step of comparing the illustrations of said device of the respective QRS complex of the transitional zone at different positions of a six lead precordial ECG horizontal plane (3,6) with the QRS complexes of a six lead V1-V6 precordial ECG measurement of said subject, such as to determine the position of the transitional zone in said six lead precordial ECG measurement. As a next step, one may then conduct the method(s) as described herein above.

Specifically, the device is used to identify which one of the precordial electrode is the position of the transitional zone, at which position the amplitudes of R and S waves look to be most similar in size to each other. Then the device is moved on the electrocardiogram so, that the QRS complex of the corresponding electrode of the device (3) is on the QRS complex of the ECG. If visually cannot be clearly decided whether the R and S waves are equal, or not, the transition zone is defined to be at this electrode. If the R wave is clearly bigger, the transition zone is between this and the next electrode clockwise, and if the S wave is clearly bigger, is the transition zone between this and the previous electrode counterclockwise.

Figure 6:
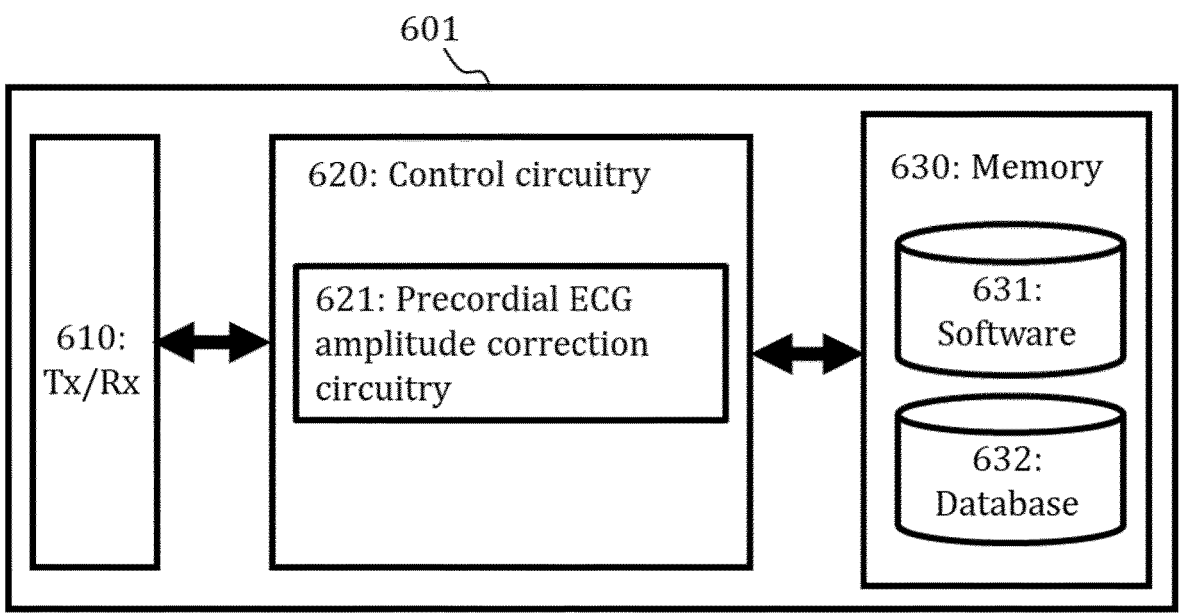
FIG. 6 illustrates an apparatus according to an embodiment.

FIG. 6 provides an apparatus 601 (e.g., a computing device) according to some embodiments. FIG. 6 may illustrate an apparatus configured to carry out at least functions described above in connection with determining a subject's corrected precordial ECG amplitude in an ECG measurement. The apparatus 601 may comprise one or more control circuitry 620, such as at least one processor, and at least one memory 630, including one or more algorithms 631, such as a computer program code (software) wherein the at least one memory and the computer program code (software) are configured, with the at least one processor, to cause, respectively, the apparatus to carry out any one of the exemplified functionalities relating to determining a subject's corrected precordial ECG amplitude in an ECG measurement as described above.

Referring to FIG. 6, the control circuitry 620 of the apparatus 601 comprises at least precordial ECG amplitude correction circuitry 621. The precordial ECG amplitude correction circuitry 621 may be configured to carry out at least some of the functionalities described above by means of any of FIGS. 3 to 5 using one or more individual circuitries.

The at least one memory 630 may comprise at least one database 632 which may comprise, for example, subject's ECG data obtainable from the first ECG measurement made at the first time point, the first ECG measurement, subject's ECG data obtainable from the second ECG measurement made at the second time point, the second ECG measurement, the first BMI value of a subject, the second BMI value of said subject, said subject's corrected precordial ECG amplitude and/or any other information used and/or produced in calculations according to embodiments.

Each memory 630 may comprise software 631 and at last one database 632. The memory 630 may also comprise other databases which may not be related to the functionalities of the apparatus according to any of presented embodiments. The at least one memory 630 may be implemented using any suitable data storage technology, such as semiconductor-based memory devices, flash memory, magnetic memory devices and systems, optical memory devices and systems, fixed memory and removable memory.

Referring to FIG. 6, the apparatus 601 may further comprise different interfaces 610 such as one or more communication interfaces (TX/RX) comprising hardware and/or software for realizing communication connectivity over one or more communications network according to one or more communication protocols. The one or more communication interfaces 610 may comprise standard well-known components such as an amplifier, filter, frequency-converter, analog-to-digital converts, (de)modulator, and encoder/decoder circuitries, controlled by the corresponding controlling units, and one or more antennas. The interfaces 610 may comprise a user input interface and/or an interface for a display.

As used in this application, the term 'circuitry' may refer to one or more or all of the following: (a) hardware-only circuit implementations, such as implementations in only analog and/or digital circuitry, and (b) combinations of hardware circuits and software (and/or firmware), such as (as applicable): (i) a combination of analog and/or digital hardware circuit(s) with software/firmware and (ii) any portions of hardware processor(s) with software, including digital signal processor(s), software, and memory(ies) that work together to cause an apparatus, such as a terminal device or an access node, to perform various functions, and (c) hardware circuit(s) and processor(s), such as a microprocessor(s) or a portion of a microprocessor(s), that requires software (e.g. firmware) for operation, but the software may not be present when it is not needed for operation. This definition of 'circuitry' applies to all uses of this term in this application, including any claims. As a further example, as used in this application, the term 'circuitry' also covers an implementation of merely a hardware circuit or processor (or multiple processors) or a portion of a hardware circuit or processor and its (or their) accompanying software and/or firmware. The term 'circuitry' also covers, for example and if applicable to the particular claim element, a baseband integrated circuit for an access node or a terminal device or other computing or network device.

In embodiments, the at least one processor, the memory, and the computer program code form processing means or comprises one or more computer program code portions for carrying out one or more operations according to any one of the embodiments of FIGS. 3 to 5 or operations thereof.

In an embodiment, at least some of the processes described in connection with of FIGS. 3 to 5 may be carried out by an apparatus comprising corresponding means for carrying out at least some of the described processes. Some example means for carrying out the processes may include at least one of the following: detector, processor (including dual-core and multiple-core processors), digital signal processor, controller, receiver, transmitter, encoder, decoder, memory, RAM, ROM, software, firmware, display, user interface, display circuitry, user interface circuitry, user interface software, display software, circuit, antenna, antenna circuitry, and circuitry. In an embodiment, the at least one processor, the memory, and the computer program code form (processing) means or comprises one or more computer program code portions for carrying out one or more operations according to any one of the embodiments of FIGS. 3 to 5 or operations thereof.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FP-GAs), processors, controllers, micro-controllers, microprocessors, other electronic units designed to perform the functions described herein, or a combination thereof. For firmware or software, the implementation can be carried out through modules of at least one chipset (procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, etc., described with regard thereto, and they are not limited to the precise configurations set forth in the given figures, as will be appreciated by one skilled in the art.

Embodiments as described may also be carried out in the form of a computer process defined by a computer program or portions thereof. Embodiments of the methods described in connection with FIGS. 3 to 5 may be carried out by executing at least one portion of a computer program comprising corresponding instructions. The computer program may be provided as a computer readable medium comprising program instructions stored thereon or as a nontransitory computer readable medium comprising program instructions stored thereon. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The computer program medium may be, for example but not limited to, a record medium, computer memory, read-only memory, electrical carrier signal, telecommunications signal, and software distribution package, for example. The computer program medium may be a non-transitory medium. Coding of software for carrying out the embodiments as shown and described is well within the scope of a person of ordinary skill in the art.

The above disclosed methods, and the use of the device of the present disclosure in such methods, will become more apparent in light of the following examples.

EXAMPLES

Example 1

For a person with a BMI of 27 and a normal transition zone, the Sokolow-Lyon (S-L) index of left ventricular electrocardiographic hypertrophy (SV1+RV5 or EV6) is determined to be 3.2 mV. Such a value is below the borderline of electrocardiographic left ventricular hypertrophy (3.5).

The same person comes to a follow-up control after one year. The measured index is 3.2 mV, which would be considered healthy.

However, the person has gained 15 kg in body weight, and the person's BMI is now 32. Looking on the device of the present disclosure, the user assigns a B1 correction value of 10%, and a B2 correction value of 25%. The difference B2-B1 is thus 15%. Since the person gained weight, i.e. showed an increase in BMI, said value is positive. Thus, the correction percentage for increase in BMI is 15%.

At the same time, by comparing the QRS complexes provided on the device with the ECG data, it is found that the transitional zone has changed from normal to V4. The user assigns to this finding a correction percentage of 10%.

In sum, the correction percentage is 15%+10%=25%, which is 0.8 mV of 3.2 mV. Accordingly, the actual S-L index is 3.2 mV+0.8 mV=4.0 mV, which is exceeding the threshold of electrocardiographic left ventricular hypertrophy (3.5).

Example 2

A subject with a previous Sokolow-Lyon index of 2.7 mV and BMI of 34 comes to a follow-up visit and the Sokolow-Lyon index is now 3.6 mV. Such a value would traditionally be considered above the threshold indicative for left ventricular hypertrophy. In order to predict the actual risk of cardiovascular diseases for this subject, the physician can check the measured ECG amplitude for accuracy.

The subject has lost weight by 30 kg and now has a BMI of 24. Using the method and device disclosed herein, the physician sees, that the percentage correction is 5%-30%=−25%. Besides, the physician sees that the position of the transition zone has changed to the no rotation area (percentage correction 0%) from the area on V4 (to which a percentage correction of 10% is assigned to), such that the difference is −10%. Thus, the total correction percentage is −25%+−10%=−35%. Hence, the corrected Sokolow-Lyon index is 3.6+(3.6×−35%)=2.34, which is below the threshold of electrocardiographic left ventricular hypertrophy (3.5). About ⅓ of the increase in the measured, uncorrected Sokolow-Lyon index is due to the lost in weight, and there is no practical difference when considering the corrected amplitude.

It will be obvious to a person skilled in the art that, as the technology advances, the inventive concept can be implemented in various ways. The invention and its embodiments are not limited to the examples described above but may vary within the scope of the claims.

REFERENCES

1. Kliegfield P G et al.: Recommendations for the standardization and interpretation of electrocardiogram. J Am Coll Cardiol. 2007; 49: 1109-27.

2. Schijvenaars B J A et al.: Intraindividual variability in electrocardiograms. J Electrocardiol. J Electrocardiol 2008; 41: 190-196.

3. van Oosterom A et al.: Geometrical factors affecting the interindividual variability of the ECG and VCG. J Electrocardiol. 2000; 33: 219-227.

4. Fowler N B et Braunstein J R.: Anatomic and electrocardiographic position of the heart. Circulation 1951; 3: 906-910.

5. Tahara Y et al.: Evaluation of the electrocardiographic transitional zone by cardiac computer tomography. J Electrocardiol. 1991; 24: 239-45.

6. Bradford N et al. Abnormal electrocardiographic QRS transition zone and risk of mortality in individuals free of cardiovascular disease. Europace 2015; 17: 131-136.

7. Patel S et al.: Counterclockwise and clockwise rotation of QRS transition zone: prospective correlates of change and time-varying associations with cardiovascular outcomes. J Am Heart Assoc. 2017; 6: 1-9.

8. Prineas R J et al: Distribution and determinants of QRS rotation of black and white persons in the general population. J Electrocardiol 2018; 51: 316-322.

9. Okin P M et al.: Effect of obesity on electrocardiographic left ventricular hypertrophy in hyperensive patients. Hypertension 2000; 35: 13-18.

10. Abacherli R et al.: Correlation relationship assessment between left ventricular hypertrophy voltage criteria and body mass index in 41,806 swiss conscripts. Ann Non-invasive Electrocardiol 2009; 14: 381-388.

11. Kurisu S et al.: Electrocardiographic characteristics in the underweight and obese in accordance with the World Health Organization classification. 2015; IJC Metabolic § Endocrine 2015; 9: 61-.

12. Rider et al.: Improvement in ECG accuracy for diagnosis of left ventricular hypertrophy in obesity. Heart 2016; 102: 1566-1572.

13. Nakamura Y.: Prognostic values of clockwise and counterclockwise rotation for cardiovascular mortality in Japanese subjects. A 24-year follow-up of the national integrated project for prospective observation of noncommunicable disease and its trends in the aged. 1980-2004 (NIPPON DATA 80). Circulation. 2012; 125: 1226-1233.

14. Hassing G J et al. Body mass index related electrocardiographic findings in healthy young individuals with a normal body mass index. Neth Heart J 2019; 27: 506-512.

15. Horton J D et al.: Distance correction for precordial electrocardiographic voltage in estimating left ventricular mass. Circulation 1977; 55: 509-512.

16. Cuspidi C et al.: Does QRS voltage correction by body mass index improve the accuracy of electrocardiography in detecting left ventricular hypertrophy and predicting cardiovascular events in general population? The Journal of Clinical Hypertension 2016; 5: 415-421.

17. Snelder S, van d Poll S, de Groot L et al.: Optimized electrocardiographic criteria for the detection of left ventricular hypertrophy in obesity patients. Clin Cardiol. 2020; 43: 483-490.

18. Norman J E et al.: Improved detection of echocardiographic left ventricular hypertrophy using a new electrocardiographic algorithm. J Am Coll Cardiol. 1993; 21: 1680-6.

19. Sathananthan G et al.: Cardiac orientation: is there a correlation between the anatomical and the electrical axis of the heart. The British Journal of Cardiology 2015; 22: 1-10.

20. Tafeit E et al.: Using body mass index ignores the intensive training of elite special force personnel. Experimental Biology and Medicine 2019; 244: 873-879.
21. Fontana L and Hu F B.: Optimal body weight for health and longevity: bridging basic, clinical and population research. Aging Cell 2014; 13: 391-400.
22. WO 2021/110937

The invention claimed is:

1. An apparatus (601) for determining a subject's corrected precordial ECG amplitude in an ECG measurement, comprising:

at least one processor (620), and at least one memory (630) for storing instructions (631) to be executed by the at least one processor (620), wherein the at least one memory (630) and the instructions are configured to, with the at least one processor (620), cause the apparatus (601) at least to perform:

maintaining (301), in said at least one memory, said subject's ECG data obtained from a first ECG measurement made at a first time point, wherein said ECG was recorded using a standardized and reproducible electrode placement method, and wherein said ECG data comprises data for a six lead V1-V6 precordial ECG;

maintaining (302), in said at least one memory, said subject's ECG data obtained from a second ECG measurement made at a second time point, which is after the first time point, wherein said ECG was recorded using a standardized and reproducible electrode placement method, and wherein said ECG data comprises data for a six lead V1-V6 precordial ECG and a precordial ECG amplitude A;

determining (303) a percentage correction value R by determining the position of the transition zone in said data of a six lead V1-V6 precordial ECG from said first ECG measurement and assigning (303) to it a percentage correlation value R1, and determining (303) the position of the transition zone in said data of a six lead V1-V6 precordial ECG from said second ECG measurement and assigning (303) to it a percentage correlation value R2, wherein R1 or R2 is independently (i) about −30% in case the transition zone is between lead V1 and lead V2, (ii) about −20% in case the transition zone is around lead V2, (iii) about −10% in case the transition zone is between lead V2 and lead V3, (iv) about 0 in case the transition zone is around lead V3 or between lead V3 and lead V4, (v) about 10% in case the transition zone is around lead V4, (vi) about 20% in case the transition zone is between lead V4 and lead V5, (vii) about 30% in case the transition zone is around lead V5, and (viii) about 40% in case the transition zone is between lead V5 and lead V6; and calculating (303) the percentage correction value R using formula (1)

$$R = R2 - R1; \text{ and} \tag{1}$$

calculating (304) a subject's corrected precordial ECG amplitude A* from a precordial ECG amplitude value A from said ECG measurement from said second time point, and the percentage correction value R, using formula (2)

$$A^* = A + (R \times A); \tag{2}$$

thereby determining said subject's corrected precordial ECG amplitude in the ECG measurement; and outputting (305) said subject's corrected precordial ECG amplitude.

2. The apparatus (601) of claim 1, wherein the at least one memory (630) and the instructions (631) are configured to, with the at least one processor (620), cause the apparatus (601) to further perform:

maintaining (501), in said at least one memory, a first BMI value of a subject, wherein said first BMI value is obtained from a first time point of a first ECG measurement;

maintaining (502), in said at least one memory, a second BMI value of said subject, wherein said second BMI value is obtained from a second time point of a second ECG measurement which is after said first time point;

maintaining (503), in said at least one memory, said subject's ECG data obtained from said first ECG measurement, wherein said ECG was recorded using a standardized and reproducible electrode placement method, and wherein said ECG data comprises data for a six lead V1-V6 precordial ECG;

maintaining (504), in said at least one memory, said subject's ECG data obtained from said second ECG measurement, wherein said ECG was recorded using a standardized and reproducible electrode placement method, and wherein said ECG data comprises data for a six lead V1-V6 precordial ECG and a precordial ECG amplitude A;

determining (505) a first percentage correction value B by assigning said first BMI value a first percentage correction value B1, and said second BMI value a second percentage correction value B2, wherein B1 and B2 are independently assigned according to the following table

| BMI | B1 or B2 in % |
|---|---|
| 17 or 18 | −15 |
| 19 or 20 | −10 |
| 21 or 22 | −5 |
| 23 | 0 |
| 24 or 25 | 5 |
| 26 or 27 | 10 |
| 28 or 29 | 15 |
| 30 or 31 | 20 |
| 32 or 33 | 25 |
| 34 or 35 | 30 |
| 36 or 37 | 35 |
| 38 or 39 | 40 |
| 40 or 41 | 45 |
| 42 or 43 | 50 |
| 44 or 45 | 55 |
| 46 or 47 | 60 |
| 48 or 49 | 65 |
| 50 or 51 | 70, | and calculating (505) the percentage correction value B using formula (3)

$$B = B2 - B1; \qquad (3)$$

determining (506) a second percentage correction value R by determining the position of the transition zone in said data of a six lead V1-V6 precordial ECG from said first ECG measurement and assigning (506) to it a percentage correlation value R1, and determining (506) the position of the transition zone in said data of a six lead V1-V6 precordial ECG from said second ECG measurement and assigning (506) to it a percentage correlation value R2, wherein R1 or R2 is independently (i) about −30% in case the transition zone is between lead V1 and lead V2, (ii) about −20% in case the transition zone is around lead V2, (iii) about −10% in case the transition zone is between lead V2 and lead V3, (iv) about 0 in case the transition zone is around lead V3 or between lead V3 and lead V4, (v) about 10% in case the transition zone is around lead V4, (vi) about 20% in case the transition zone is between lead V4 and lead V5, (vii) about 30% in case the transition zone is around lead V5, and (viii) about 40% in case the transition zone is between lead V5 and lead V6; and calculating (506) the percentage correction value R using formula (1)

$$R = R2 - R1; \text{ and} \qquad (1)$$

calculating (507) a subject's corrected precordial ECG amplitude A* from a precordial ECG amplitude value A from said second ECG measurement using formula (5)

$$A^* = A + [(B + R) \times A]; \qquad (5)$$

thereby determining a subject's corrected precordial ECG amplitude from an ECG measurement; and outputting (508) said subject's corrected precordial ECG amplitude.

3. The apparatus (601) according to claim 1, wherein the at least one memory (630) and the instructions (631) are configured to, with the at least one processor (620), cause the apparatus (601) to perform the outputting (305, 508) by:

causing displaying said subject's corrected precordial ECG amplitude in the ECG measurement to a user via a display comprised in or electrically connected to the apparatus; or outputting said subject's corrected precordial ECG amplitude in the ECG measurement to a second apparatus for displaying said subject's corrected precordial ECG amplitude in the ECG measurement to a user, wherein said second apparatus is connected to the apparatus via at least one communication link and/or at least one communication network.

4. A computer program product, embodied on a non-transitory computer readable medium, comprising program instructions, that when run is adapted to determine a subject's corrected precordial ECG amplitude in an ECG measurement by performing:

maintaining (301), in said at least one memory, said subject's ECG data obtained from a first ECG measurement made at a first time point, wherein said ECG data was recorded using a standardized and reproducible electrode placement method, and wherein said ECG data comprises data for a six lead V1-V6 precordial ECG;

maintaining (302), in said at least one memory, said subject's ECG data obtained from a second ECG measurement made at a second time point, which is after the first time point, wherein said ECG was recorded using a standardized and reproducible electrode placement method, and wherein said ECG data comprises data for a six lead V1-V6 precordial ECG and a pre-cordial ECG amplitude A;

determining (303) a percentage correction value R by determining the position of the transition zone in said data of a six lead V1-V6 precordial ECG from said first ECG measurement and assigning (303) to it a percentage correlation value R1, and determining (303) the position of the transition zone in said data of a six lead V1-V6 precordial ECG from said second ECG measurement and assigning (303) to it a percentage correlation value R2, wherein R1 or R2 is independently (i) about −30% in case the transition zone is between lead V1 and lead V2, (ii) about −20% in case the transition zone is around lead V2, (iii) about −10% in case the transition zone is between lead V2 and lead V3, (iv) about 0 in case the transition zone is around lead V3 or between lead V3 and lead V4, (v) about 10% in case the transition zone is around lead V4, (vi) about 20% in case the transition zone is between lead V4 and lead V5, (vii) about 30% in case the transition zone is around lead V5, and (viii) about 40% in case the transition zone is between lead V5 and lead V6; and calculating (303) the percentage correction value R using formula (1)

$$R = R2 - R1; \text{ and} \qquad (1)$$

calculating (304) a subject's corrected precordial ECG amplitude A* from a precordial ECG amplitude value A from said ECG measurement from said second time point, and the percentage correction value R, using formula (2)

$$A^* = A + (R \times A); \qquad (2)$$

thereby determining said subject's corrected precordial ECG amplitude in the ECG measurement; and causing (305) outputting said subject's corrected precordial ECG amplitude.

*    *    *    *    *